US012643899B2

(12) United States Patent
Jean et al.

(10) Patent No.: US 12,643,899 B2
(45) Date of Patent: Jun. 2, 2026

(54) ANTIVIRAL AGENTS, USES THEREOF AND METHODS FOR THEIR PREPARATION

(71) Applicant: The University of British Columbia, Vancouver (CA)

(72) Inventors: François Jean, Vancouver (CA); Raymond Andersen, Vancouver (CA); David Williams, Vancouver (CA); Julian Davies, Vancouver (CA); Rory Long, Barcelona (ES); Tirosh Shapira, Vancouver (CA); Weeda Morsal Mamozai, Oberasbach (DE); Luka Krampert, Regensburg (DE)

(73) Assignee: The University of British Columbia, Vancouver (CA)

( * ) Notice: Subject to any disclaimer, the term of this patent is extended or adjusted under 35 U.S.C. 154(b) by 653 days.

(21) Appl. No.: 17/920,315

(22) PCT Filed: Apr. 23, 2021

(86) PCT No.: PCT/CA2021/050559
§ 371 (c)(1),
(2) Date: Oct. 20, 2022

(87) PCT Pub. No.: WO2021/212234
PCT Pub. Date: Oct. 28, 2021

(65) Prior Publication Data

US 2023/0167115 A1 Jun. 1, 2023

Related U.S. Application Data

(60) Provisional application No. 63/038,248, filed on Jun. 12, 2020, provisional application No. 63/015,027, filed on Apr. 24, 2020.

(51) Int. Cl.
*C07D 471/22* (2006.01)
*A61P 31/14* (2006.01)

(52) U.S. Cl.
CPC ............ *C07D 471/22* (2013.01); *A61P 31/14* (2018.01)

(58) Field of Classification Search
CPC ............................... C07D 471/22; A61P 31/14
See application file for complete search history.

(56) References Cited

U.S. PATENT DOCUMENTS

2011/0038852 A1 2/2011 Meldrum et al.

FOREIGN PATENT DOCUMENTS

| | | |
|---|---|---|
| FR | 2845995 | 4/2004 |
| WO | WO 2001/087887 A2 | 11/2001 |
| WO | WO 2017/004568 A1 | 1/2017 |
| WO | 2019/182947 | 9/2019 |

OTHER PUBLICATIONS

Chang & Brady, (2013) "Discovery of indolotryptoline antiproliferative agents by homology-guided metagenomic screening", Proceedings of the National Academy of Sciences, vol. 110, No. 7, pp. 2478-2483.
Du & Ryan, (2016) "Catalytic repertoire of bacterial bisindole formation" Current Opinion in Chemical Biology, vol. 31, pp. 74-81.
Duan et al., (2008) "Novel binding between pre-membrane protein and vacuolar ATPase is required for efficient dengue virus secretion", Biochemical and Biophysical Research Communications, vol. 373, No. 2, pp. 319-324.
Ferry et al., (2011) "Characterization of novel Checkpoint kinase 1 inhibitors by in vitro assays and in human cancer cells treated with topoisomerase inhibitors" Life Sciences, vol. 89, No. 7-8, pp. 259-268.
Guinea & Carrasco, (1995) "Requirement for vacuolar proton-ATPase activity during entry of influenza virus into cells" Journal of Virology, vol. 69, No. 4, pp. 2306-2312.
Hu et al., (2017) "Nanoparticulate vacuolar ATPase blocker exhibits potent host-targeted antiviral activity against feline coronavirus" Scientific Reports, vol. 7, No. 1, 13043., pp. 5965-5980.
Hugon et al., (2007) "Synthesis and biological activities of isogranulatimide analogues", Bioorganic & Medicinal Chemistry, vol. 15, No. 17, pp. 5965-5980.
Molina-Ruiz et al., (2009) "A TOPological Sub-structural Molecular Design (TOPS-MODE)-QSAR approach for modeling the antiproliferative activity against murine leukemia tumor cell line (L1210)" Bioorganic & Medicinal Chemistry, vol. 17, No. 2, pp. 537-547.
Montiel et al., (2015) "Yeast homologous recombination-based promoter engineering for the activation of silent natural product biosynthetic gene clusters" Proceedings of the National Academy of Sciences, vol. 112, No. 29, pp. 8953-8958.

(Continued)

*Primary Examiner* — Alicia L Otton
(74) *Attorney, Agent, or Firm* — Rudy J. Ng; Bozicevic, Field & Francis LLP

(57) ABSTRACT

The present disclosure relates to the use of antiviral agents that are cladoniamides and derivatives thereof such as the compound Formula I, for example, for the treatment of viral infections such as those caused by coronaviruses and/or flaviviruses. The present disclosure also includes antiviral agents and methods for their preparation.

I

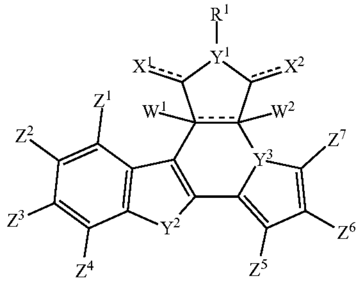

22 Claims, 18 Drawing Sheets

(56) References Cited

OTHER PUBLICATIONS

Nawa, (1997) "Japanese Encephalitis Virus Infection in Vero Cells: The Involvement of Intracellular Acidic Vesicles in the Early Phase of Viral Infection Was Observed with the Treatment of a Specific Vacuolar Type H+-ATPase Inhibitor, Bafilomycin A1", Microbiology and Immunology, vol. 41, No. 7, pp. 537-543.
Ou et al., (2020) "Characterization of spike glycoprotein of SARS-CoV-2 on virus entry and its immune cross-reactivity with SARS-CoV" Nature Communications, vol. 11, No. 1, 1620.
Regan et al., (2008) "Differential role for low pH and cathepsin-mediated cleavage of the viral spike protein during entry of serotype II feline coronaviruses" Veterinary Microbiology, vol. 132, No. 3-4, pp. 235-248.
Ryan, (2011) "Biosynthetic Gene Cluster for the Cladoniamides, Bis-Indoles with a Rearranged Scaffold", PLoS ONE, vol. 6, No. 8, e23694.
Yang & Shen, (2020) "Targeting the Endocytic Pathway and Autophagy Process as a Novel Therapeutic Strategy in COVID-19" International Journal of Biological Sciences, vol. 16, No. 10, pp. 1724-1731.
Chang et al., (2011) "Cloning and Characterization of an Environmental DNA-Derived Gene Cluster That Encodes the Biosynthesis of the Antitumor Substance BE-54017.", J. Am. Chem. Soc., vol. 133, No. 26, pp. 9996-9999.
Chang et al., (2014) "Mutations in the Proteolipid Subunits of the Vacuolar H+-ATPase Provide Resistance to Indolotryptoline Natural Products", Biochemistry, American Chemical Society, 53, 7123-7131.
Deng et al., (2015) "Reduced Deformability of Parasitized Red Blood Cells as a Biomarker for Anti-Malarial Drug Efficacy", Malar J., 14:428, 9 pages.
Deng et al., (2016) "Adenosine Analog NITD008 Is a Potent Inhibitor of Zika Virus", Open Forum Infectious Diseases, 4 pages.
Deslandes et al., (2012) "Synthesis and Biological Evaluation of Analogs of the Marine Alkaloids Granulatimide and Isogranulatimide", Eur. J. Med. Chern., vol. 54, pp. 626-636.
Du et al., (2014) "Reconstruction of Cladoniamide Biosynthesis Reveals Nonenzymatic Routes 30 to Bisindole Diversity." ACS Chemical Biology, vol. 9, No. 12, pp. 2748-2754.
Du & Ryan (2015) "Expansion of Bisindole Biosynthetic Pathways by Combinatorial Construction", ACS Synth Biol., 15 pages.
Duncan et al., (2020) "Virtual Screening Identifies Chebulagic Acid as an Inhibitor of the M2(S31N) Viral Ion Channel and Influenza A Virus." Molecules, vol. 25, No. 2903, 17 pages.
Hofmann et al., (2004) "S Protein of Severe Acute Respiratory Syndrome-Associated Coronavirus Mediates Entry Into Hepatoma Cell Lines and Is Targeted by Neutralizing Antibodies in Infected Patients", Journal of Virology, vol. 78 (12): 6134-6142.
Hudkins et al., (1995) "Synthesis Of 2-Aryl- and 2-Vinyl-lff-indoles via Palladium-Catalyzed Cross-Coupling of Aryl and Vinyl Halides with -Carboxy-2-(tributylstannyl)indole", J. Org. Chem. 60, 6218-6220.
Hyrina et al., (2017) "Human Subtilisin Kexin Isozyme-1 (SKI-1)/Site-1 Protease (S1P) Regulates Cytoplasmic Lipid Droplet Abundance: A Potential Target for Indirect-Acting Anti-Dengue Virus Agents", PLOS ONE, 22 pages.
Kimura et al., (2012) "Synthesis and Assignment of the Absolute Configuration of Indenotryptoline Bisindole Alkaloid BE-540 17", Org. Lett., vol. 14, No. 17, pp. 4418-4421.
Lin et al., (2005) "Binding interaction of SARS Coronavirus 3CLpro Protease with Vacuolar-H+ ATPase G1 Subunit", FEBS Letters 579:6089-6094.
Merino-Ramos et al., (2017) "Antiviral Activity of Nordihydroguaiaretic Acid and Its Derivative Tetra-O-Methyl Nordihydroguaiaretic Acid against West Nile Virus and Zika Virus", Antimicrobial Agents and Chemotherapy, vol. 61 Issue 8, 10 pages.
Muller & Milton (2012) "The Determination and Interpretation of the Therapeutic Index in Drug Development", Nature Reviews, Drug Discovery, vol. 11:751-761.
Murata et al., (2005) "Structure of the Rotor of the V-Type Naϕ-ATPase from Enterococcus hirae", Science vol. 308: 654-660.
Williams et al., (2008) "Cladoniamides A-G, Tryptophan-Derived Alkaloids Produced in Culture by *Streptomyces uncialis*", American Chemical Society, vol. 10(16):3501-3504.
Wood et al., (1997) "Design and Implementation of an Efficient Synthetic Approach to Furanosylated Indolocarbazoles: Total Synthesis of (+)- and (−)-K252a." J. Am. Chern. Soc., vol. 119, No. 41, 9641-9651.
Xie et al., (2016) "Zika Virus Replicons for Drug Discovery", EBioMedicine 12:156-160.
Kohio and Adamson (2013) "Glycolytic control of vacuolar-type ATPase activity: A mechanism to regulate influenza viral infection ," Virology,444: 301-309.

ANTIVIRAL AGENTS, USES THEREOF AND METHODS FOR THEIR PREPARATION

CROSS-REFERENCE TO RELATED APPLICATIONS

The present disclosure is a National Stage entry of International Application No. PCT/CA2021/050559, filed Apr. 23, 2021, which claims the benefit of priority from U.S. provisional application Nos. 63/015,027 filed on Apr. 24, 2020 and 63/038,248 filed on Jun. 12, 2020, the contents of all of which are incorporated herein by reference in their entirety.

TECHNICAL FIELD

The present disclosure relates to antiviral agents. For example, the present disclosure relates to cladoniamide compounds that are antiviral agents against viruses such as coronaviruses and/or flaviviruses as well as methods for their preparation and their use.

BACKGROUND

The Flaviviridae family of viruses are positive, single-stranded, enveloped ribonucleic acid (RNA) viruses found primarily in ticks and mosquitoes, which can lead to human infections. For example, members of the genus *Flavivirus* include viruses, like dengue virus (DENV), West Nile virus (WNV), Zika virus (ZIKV), Powassan virus (POWV), Japanese encephalitis virus (JEV) and yellow fever virus (YFV), which are important human pathogens. Most human flavivirus infections are incidental, since the viruses are unable to replicate the virus to high enough titers in their human host. However, there are exceptions in the case of DENV, WNV, ZIKV and YFV. For some flaviviruses, there are readily available and effective vaccines (i.e. YFV and JEV). However, there is no vaccine for ZIKV and the DENV vaccine, Dengvaxia™, which is a tetravalent chimeric vaccine that splices structural genes of the four dengue viruses onto a 17D yellow fever backbone, has proved to be less than optimal. Furthermore, because DENV, ZIKV, and WNV are all dual-host mosquito-borne flaviviruses, co-infections are common. Currently, there is no treatment for ZIKV and no specific medicine to treat DENV or WNV, so antiviral agents against flavivirus infections are needed urgently.

The Coronaviridae family of viruses are enveloped, positive-sense, single-stranded RNA viruses, which cause infectious diseases in mammals and birds. In humans, coronaviruses often cause respiratory infections, ranging from only mild symptoms, such as in the common cold, to more serious symptomatic courses such as in severe acute respiratory syndrome (SARS, first reported in 2002), Middle East respiratory syndrome (MERS, first reported in 2012), or coronavirus disease (COVID-19, first reported in 2019), which for some patients can be lethal. Currently, there are no vaccines or antiviral drugs to prevent or treat most human coronavirus infections. The alarming rate at which new coronaviruses have been emerging and spreading over the past 20 years is a reason why there exists an urgent need to find new antiviral agents useful against coronavirus infections.

SUMMARY

Cladoniamide A produced by actinomycete *Streptomyces unicialis* is active against coronavirus and flavivirus. While

*S. unicialis* also produces other cladoniamides, such as e.g. cladoniamide D, cladoniamide D possessed no activity against DENV and ZIKV. Similar results were also found for SARS-CoV-2. Cladoniamide E and cladoniamide F similarly showed no activity against ZIKV. Cladoniamide A was found to be a highly effective antiviral against the UK strain of SARS-CoV-2 (202012/01), with an $ED_{50}$ of about 800 pM. Cladoniamide A and cladoniamide C both showed anti-ZIKV activity in brain organoids infected with ZIKV.

Accordingly, the present disclosure includes a use of a compound of the Formula I or a pharmaceutically acceptable salt thereof for treatment of a viral infection in a subject in need thereof:

I

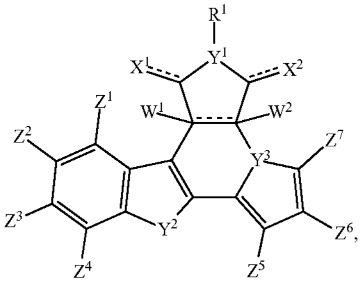

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

The present disclosure also includes a use of a compound of the Formula I or a pharmaceutically acceptable salt thereof for preparation of a medicament for treatment of a viral infection in a subject in need thereof:

I

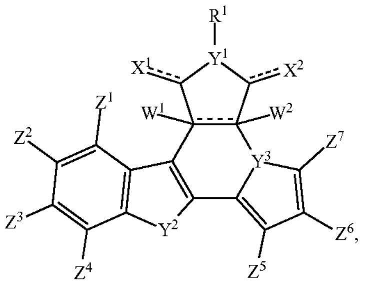

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

In an embodiment, the compound of Formula I is a compound of Formula I(a):

I(a)

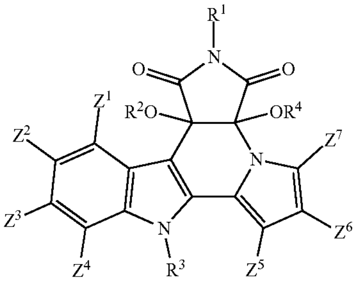

wherein $Z^1$, $Z^2$, $Z^3$, $Z^4$, $Z^5$, $Z^6$, and $Z^7$, are each independently H, halo, optionally substituted alkyl, aryl, heteroaryl, $NO_2$, NR'R", NR'$SO_2$R", CONR'R", NR'COR", OR', SR', CN, or $CF_3$; or $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$;

$R^1$, $R^2$, $R^3$, and $R^4$ are each independently H or an optionally substituted alkyl; and R' and R" are each independently H, or an optionally substituted alkyl.

In an embodiment, $R^1$ is $C_{1-6}$alkyl. In another embodiment, $R^1$ is methyl.

In an embodiment, $R^2$ and $R^4$ are both H.

In an embodiment, $R^3$ is H.

In an embodiment, $Z^5$ is OR', wherein R' is alkyl. In another embodiment, $Z^5$ is $OCH_3$.

In an embodiment, $Z^1$, $Z^3$ and $Z^4$ are all H.

In an embodiment, $Z^2$ is halo or H. In another embodiment, $Z^2$ is chloro.

In an embodiment, $Z^6$ and $Z^7$ together form a substituted aromatic ring or unsubstituted aromatic ring. In another embodiment, $Z^6$ and $Z^7$ together form an unsubstituted, 6-membered aromatic ring.

In an embodiment, the compound is a compound of Formula III:

III

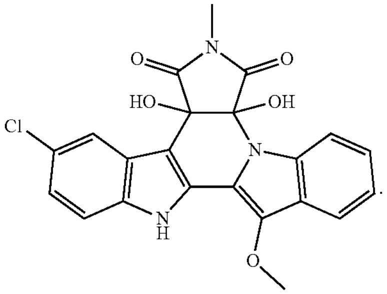

In an embodiment, the compound is cladoniamide A.

In an embodiment, the compound or the pharmaceutically acceptable salt thereof is the compound.

In an embodiment, the viral infection is caused by one or more coronavirus and/or flavivirus. In another embodiment, the viral infection is caused by one or more coronavirus. In a further embodiment, the viral infection is caused by one or more of severe acute respiratory syndrome (SARS) coronavirus-1 (SARS-CoV-1), SARS coronavirus-2 (SARS-CoV-2), Middle East respiratory syndrome (MERS) coronavirus (MERS-CoV) and human coronavirus 229E (HCoV-229E). In another embodiment, the viral infection is caused by SARS-CoV-2. In another embodiment, the SARS-CoV-2 is SARS-CoV-2 South Africa (501Y.V2), SARS-CoV-2 UK (VOC 202012/01) or SARS-CoV-2 Nigeria. In another embodiment, the viral infection is caused by HCoV-229E. In an embodiment, the viral infection is caused by one or more flavivirus. In another embodiment, the viral infection is caused by one or more of dengue virus (DENV), West Nile virus (WNV), Zika virus (ZIKV), Powassan virus (POWV), Japanese encephalitis virus (JEV) and yellow fever virus (YFV). In another embodiment, the viral infection is caused by one or more of West Nile virus (WNV), Powassan virus (POWV), Japanese encephalitis virus (JEV) and yellow fever virus (YFV). In an embodiment, the viral infection is caused by dengue virus (DENV). In an embodiment, the viral infection is caused by Zika virus (ZIKV).

In an embodiment, the subject is a human.

In an embodiment, the compound is formulated for administration in a pharmaceutical composition comprising the compound and optionally a pharmaceutically acceptable carrier.

The present disclosure also includes a compound of Formula I(b):

I(b)

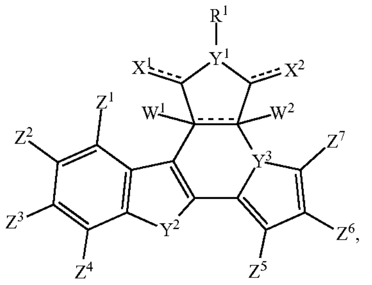

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl;

or a pharmaceutically acceptable salt thereof, with the proviso that said compound is not exactly:

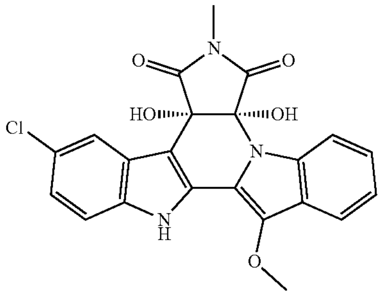

Cladoniamide A;

-continued

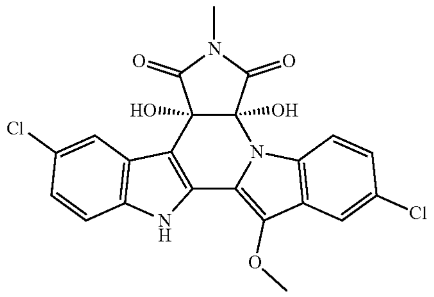

Cladoniamide B;

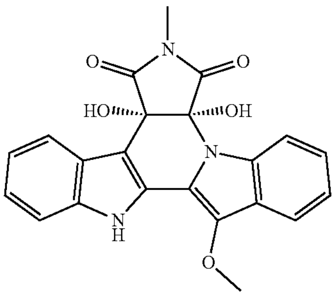

Cladoniamide C;

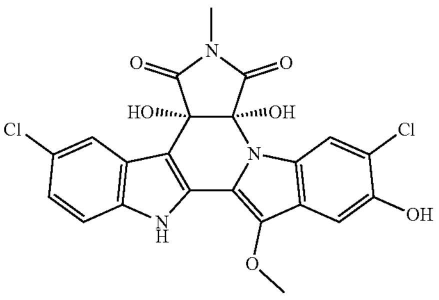

Lazarimide A;

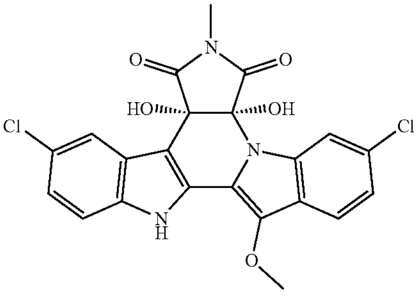

Lazarimide B;

BE-54017

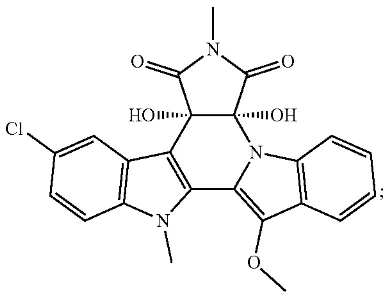

;

-continued

BE-54017'5

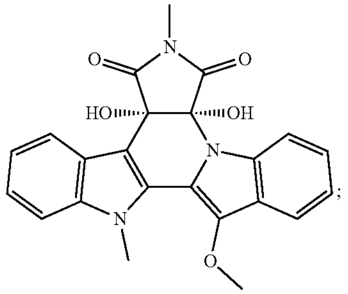

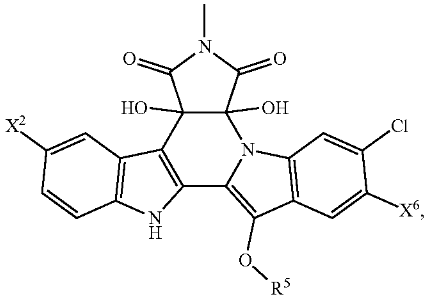

or wherein $R^5$ is $C_{1-4}$alkyl, $X^2$ is selected from H and halo, and $R^1$ is selected from H, halo and OH.

The present disclosure also includes a use of a compound of Formula I or a pharmaceutically acceptable salt thereof for inhibiting vacuolar-$H^+$ATPase (V-ATPase):

I

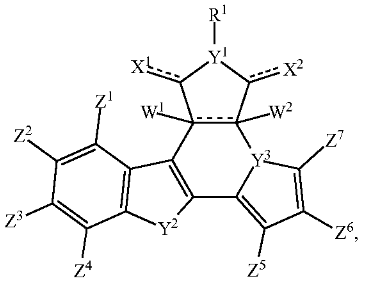

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

In an embodiment, the compound of Formula I is a compound of Formula I(a):

I(a)

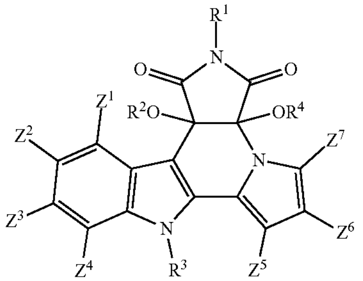

wherein $Z^1$, $Z^2$, $Z^3$, $Z^4$, $Z^5$, $Z^6$, and $Z^7$, are each independently H, halo, optionally substituted alkyl, aryl, heteroaryl, $NO_2$, NR'R", NR'$SO_2$R", CONR'R", NR'COR", OR', SR', CN, or $CF_3$; or $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$;

$R^1$, $R^2$, $R^3$, and $R^4$ are each independently H or an optionally substituted alkyl; and R' and R" are each independently H, or an optionally substituted alkyl.

In an embodiment, $R^1$ is $C_{1-6}$alkyl. In another embodiment, $R^1$ is methyl.

In an embodiment, $R^2$ and $R^4$ are both H.

In an embodiment, $R^3$ is H.

In an embodiment, $Z^5$ is OR', wherein R' is alkyl. In another embodiment, $Z^5$ is $OCH_3$.

In an embodiment, $Z^1$, $Z^3$ and $Z^4$ are all H.

In an embodiment, $Z^2$ is halo or H. In another embodiment, $Z^2$ is chloro.

In an embodiment, $Z^6$ and $Z^7$ together form a substituted aromatic ring or unsubstituted aromatic ring. In another embodiment, $Z^6$ and $Z^7$ together form an unsubstituted, 6-membered aromatic ring.

In an embodiment, the compound is a compound of Formula III:

III

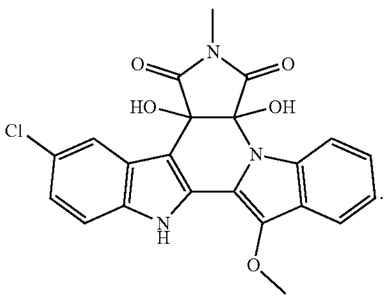

In an embodiment, the compound is cladoniamide A.

In an embodiment, the compound or the pharmaceutically acceptable salt thereof is the compound.

In an embodiment, the inhibition of V-ATPase is in a subject.

In an embodiment, the subject suffers from a viral infection.

In an embodiment, the viral infection is caused by one or more coronavirus and/or flavivirus. In another embodiment, the viral infection is caused by one or more coronavirus. In a further embodiment, the viral infection is caused by one or more of severe acute respiratory syndrome (SARS) coronavirus-1 (SARS-CoV-1), SARS coronavirus-2 (SARS-CoV-2), Middle East respiratory syndrome (MERS) coronavirus (MERS-CoV) and human coronavirus 229E (HCoV-229E). In another embodiment, the viral infection is caused by SARS-CoV-2. In another embodiment, the SARS-CoV-2 is SARS-CoV-2 South Africa (501Y.V2), SARS-CoV-2 UK (VOC 202012/01) or SARS-CoV-2 Nigeria. In another embodiment, the viral infection is caused by HCoV-229E. In an embodiment, the viral infection is caused by one or more flavivirus. In another embodiment, the viral infection is caused by one or more of dengue virus (DENV), West Nile virus (WNV), Zika virus (ZIKV), Powassan virus (POWV), Japanese encephalitis virus (JEV) and yellow fever virus (YFV). In another embodiment, the viral infection is caused by one or more of West Nile virus (WNV), Powassan virus (POWV), Japanese encephalitis virus (JEV) and yellow fever virus (YFV). In an embodiment, the viral infection is caused by dengue virus (DENV). In an embodiment, the viral infection is caused by Zika virus (ZIKV).

In an embodiment, the subject is a human.

In an embodiment, the compound is formulated for administration in a pharmaceutical composition comprising the compound and optionally a pharmaceutically acceptable carrier.

One embodiment of the present disclosure comprises the use of a compound of Formula I(a) for treatment of a viral infection:

(Formula I(a))

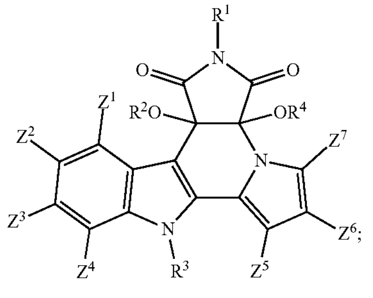

wherein $Z^1$, $Z^2$, $Z^3$, $Z^4$, $Z^5$, $Z^6$, and $Z^7$, independently may be H, halogen, an alkyl, optionally substituted, an aromatic cycle, an aromatic heterocycle, $NO_2$, NR'R", NR'$SO_2$R", CONR'R", NR'COR", OR', SR', CN, or $CF_3$; $Z^6$ and $Z^7$, optionally, may be forming an aromatic ring that, optionally, may be further substituted; and wherein $R^1$, $R^2$, $R^3$, and $R^4$, independently may be H or an, optionally substituted, alkyl; and R' and R" independently may be H, or an, optionally substituted, alkyl. Wherein said viral infection may be caused by one or more coronavirus and/or flavivirus. Wherein said viral infection may be caused by one or more coronavirus. Wherein said coronavirus may be Severe Acute Respiratory Syndrome (SARS) coronavirus-1 (SARS-CoV-1), or coronavirus-2 (SARS-CoV-2), or Middle East Respiratory Syndrome (MERS) coronavirus (MERS-CoV). Wherein said coronavirus may be SARS-CoV-2. Wherein said coronavirus may be human coronavirus 229E (HCoV-229E). Wherein said viral infection may be caused by one or more flavivirus. Wherein said viral infection may be mosquito-borne. Wherein said flavivirus may be Dengue virus (DENV), West Nile virus (WNV), Zika virus (ZIKV), Powassan virus (POWV), Japanese encephalitis virus (JEV), Yellow Fever virus (YFV), or a combination thereof.

One embodiment of the present disclosure comprises the use of a compound of Formula II(a) for treatment of a viral infection:

(Formula II(a))

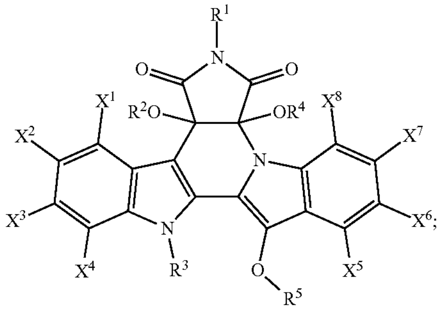

wherein $X^1$, $X^2$, $X^3$, $X^4$, $X^5$, $X^6$, $X^7$, and $X^8$ independently may be H, halogen, an alkyl, optionally substituted, an aromatic cycle, an aromatic heterocycle, $NO_2$, NR'R", NR'$SO_2$R", CONR'R", NR'COR", OR', SR', CN, or $CF_3$; $R^1$, $R^2$, $R^3$, $R^4$, and $R^5$, independently may be H or an, optionally substituted, alkyl; and R' and R" independently may be H, or an, optionally substituted, alkyl. Wherein said viral infection may be caused by one or more coronavirus and/or flavivirus. Wherein said viral infection may be caused by one or more coronavirus. Wherein said coronavirus may be Severe Acute Respiratory Syndrome (SARS) coronavirus-1 (SARS-CoV-1), or coronavirus-2 (SARS-CoV-2), or Middle East Respiratory Syndrome (MERS) coronavirus (MERS-CoV). Wherein said coronavirus may be SARS-CoV-2. Wherein said coronavirus may be human coronavirus 229E (HCoV-229E). Wherein said viral infection may be caused by one or more flavivirus. Wherein said viral infection may be mosquito-borne. Wherein said flavivirus may be Dengue virus (DENV), West Nile virus (WNV), Zika virus (ZIKV), Powassan virus (POWV), Japanese encephalitis virus (JEV), Yellow Fever virus (YFV), or a combination thereof.

A further embodiment the present disclosure comprises the use of a compound of Formula III for the treatment of a viral infection:

(Formula III)

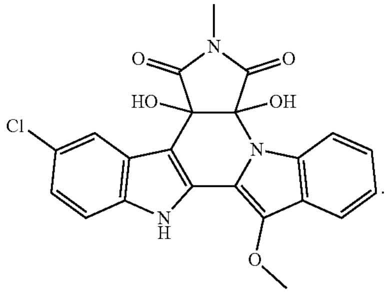

Wherein said viral infection may be caused by one or more coronavirus and/or flavivirus. Wherein said viral infection may be caused by one or more coronavirus. Wherein said coronavirus may be Severe Acute Respiratory Syndrome (SARS) coronavirus-1 (SARS-CoV-1), or coronavirus-2 (SARS-CoV-2), or Middle East Respiratory Syndrome (MERS) coronavirus (MERS-CoV). Wherein said coronavirus may be SARS-CoV-2. Wherein said coronavirus may be human coronavirus 229E (HcoV-229E). Wherein said viral infection may be caused by one or more flavivirus. Wherein said viral infection may be mosquito-borne. Wherein said flavivirus may be Dengue virus (DENV), West Nile virus (WNV), Zika virus (ZIKV), Powassan virus (POWV), Japanese encephalitis virus (JEV), Yellow Fever virus (YFV), or a combination thereof. Wherein said viral infection may be caused by DENV or ZIKV, or a combination thereof.

One embodiment of the present disclosure comprises the use of cladoniamide A for treatment of a flavivirus infection. Wherein said cladoniamide A has a chemical structure of Formula III(a):

(Formula III(a))

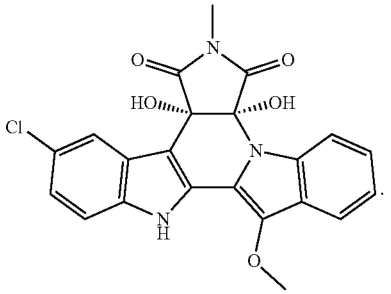

Wherein said flavivirus may be Dengue virus (DENV), West Nile virus (WNV), Zika virus (ZIKV), Powassan virus (POWV), Japanese encephalitis virus (JEV), Yellow Fever virus (YFV), or a combination thereof. Wherein said flavivirus may be DENV or ZIKV, or a co-infection thereof. Wherein said flavivirus may be DENV-3. Wherein said flavivirus may be DENV-4. Wherein said flavivirus may be ZIKV.

Another embodiment of the present disclosure comprises the use of cladoniamide A for treatment of a coronavirus infection. Wherein said cladoniamide A has a chemical structure of Formula III(a):

(Formula III(a))

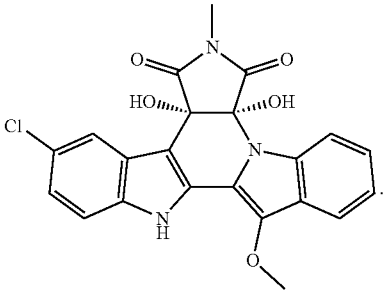

Wherein said viral infection may be caused by one or more coronavirus. Wherein said coronavirus may be Severe Acute Respiratory Syndrome (SARS) coronavirus-1 (SARS-CoV-1), or coronavirus-2 (SARS-CoV-2), or Middle East Respiratory Syndrome (MERS) coronavirus (MERS-CoV). Wherein said coronavirus may be SARS-CoV-2. Wherein said coronavirus may be human coronavirus 229E (HcoV-229E).

A further embodiment of the present disclosure comprises the use of ent-cladoniamide A for treatment of a flavivirus infection. Wherein said ent-cladoniamide A has a chemical structure of Formula III (b):

(Formula III(b))

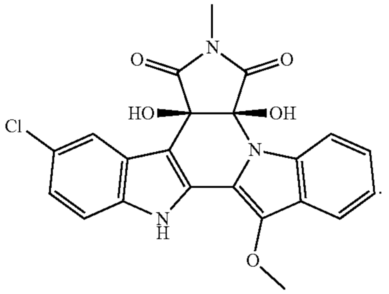

Wherein said flavivirus may be Dengue virus (DENV), West Nile virus (WNV), Zika virus (ZIKV), Powassan virus (POWV), Japanese encephalitis virus (JEV), Yellow Fever virus (YFV), or a combination thereof.

A further embodiment of the present disclosure comprises the use of ent-cladoniamide A for treatment of a coronavirus infection, wherein said ent-cladoniamide A has a chemical structure of Formula III(b):

(Formula III(b))

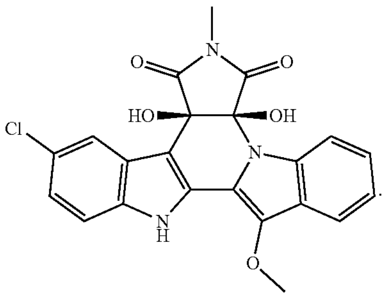

Wherein said viral infection may be caused by one or more coronavirus. Wherein said coronavirus may be Severe Acute Respiratory Syndrome (SARS) coronavirus-1 (SARS-CoV-1), or coronavirus-2 (SARS-CoV-2), or Middle East Respiratory Syndrome (MERS) coronavirus (MERS-CoV). Wherein said coronavirus may be SARS-CoV-2. Wherein said coronavirus may be human coronavirus 229E (HcoV-229E).

One embodiment of the present disclosure provides a method of use of a compound of Formula I(a) for inhibiting vacuolar-$H^+$ATPase (V-ATPase):

(Formula I(a))

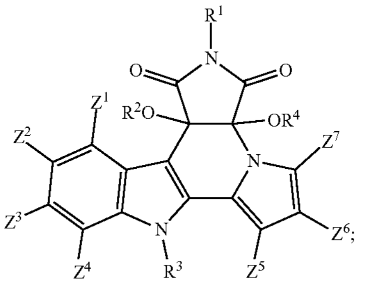

wherein $Z^1$, $Z^2$, $Z^3$, $Z^4$, $Z^5$, $Z^6$, and $Z^7$, independently may be H, halogen, an alkyl, optionally substituted, an aromatic cycle, an aromatic heterocycle, $NO_2$, NR'R", NR'$SO_2$R", CONR'R", NR'COR", OR', SR', CN, or $CF_3$; $Z^6$ and $Z^7$, optionally, may be forming an aromatic ring that, optionally, may be further substituted; and wherein $R^1$, $R^2$, $R^3$, and $R^4$, independently may be H or an, optionally substituted, alkyl; and R' and R" independently may be H, or an, optionally substituted, alkyl, said method comprising: providing a compound of Formula I(a) to a subject in need of V-ATPase inhibition. Wherein said subject may be a human or an animal. Wherein said subject may suffer from a viral infection. Wherein said viral infection may be a coronavirus infection. Wherein said viral infection may be caused by one or more coronavirus. Wherein said coronavirus may be Severe Acute Respiratory Syndrome (SARS) coronavirus-1 (SARS-CoV-1), or coronavirus-2 (SARS-CoV-2), or Middle East Respiratory Syndrome (MERS) coronavirus (MERS-CoV). Wherein said coronavirus may be SARS-CoV-2. Wherein said coronavirus may be human coronavirus 229E (HcoV-229E). Wherein said viral infection may be a flavivirus infection. Wherein said flavivirus may be Dengue virus (DENV), West Nile virus (WNV), Zika virus (ZIKV), Powassan virus (POWV), Japanese encephalitis virus (JEV), Yellow Fever virus (YFV), or a combination thereof. Wherein said viral infection may be DENV or ZIKV, or a combination thereof.

One embodiment of the present disclosure comprises a compound of Formula I(a):

(Formula I(a))

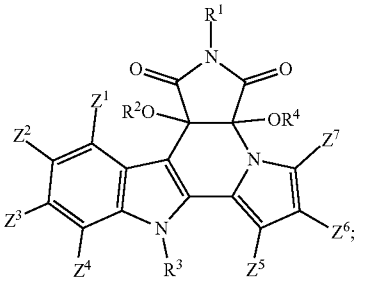

wherein $Z^1$, $Z^2$, $Z^3$, $Z^4$, $Z^5$, $Z^6$, and $Z^7$, independently may be H, halogen, an alkyl, optionally substituted, an aromatic cycle, an aromatic heterocycle, $NO_2$, NR'R", NR'$SO_2$R", CONR'R", NR'COR", OR', SR', CN, or $CF_3$; $R^1$, $R^2$, $R^3$, and $R^4$, independently may be H or an, optionally substituted, alkyl; and R' and R" independently may be H, or an, optionally substituted, alkyl.

Another embodiment of the present disclosure comprises a compound of Formula II(b):

(Formula II(b))

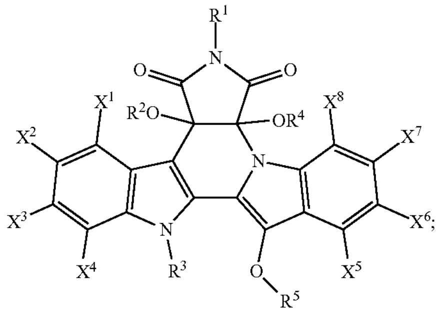

wherein $X^1$, $X^2$, $X^3$, $X^4$, $X^5$, $X^6$, $X^7$, and XV independently may be H, halogen, an alkyl, optionally substituted, an aromatic cycle, an aromatic heterocycle, $NO_2$, NR'R", NR'$SO_2$R", CONR'R", NR'COR", OR', SR', CN, or $CF_3$; $R^1$, $R^2$, $R^3$, $R^4$, and $R^5$, independently may be H or an, optionally substituted, alkyl; and R' and R" independently may be H, or an, optionally substituted, alkyl with the proviso that said compound is not exactly:

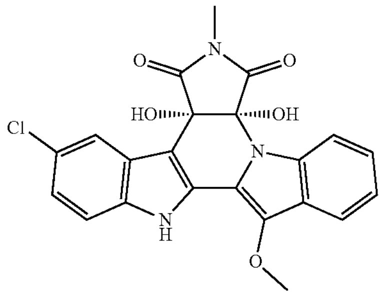

Cladoniamide A;

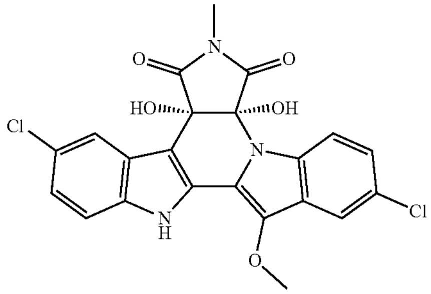

Cladoniamide B;

-continued

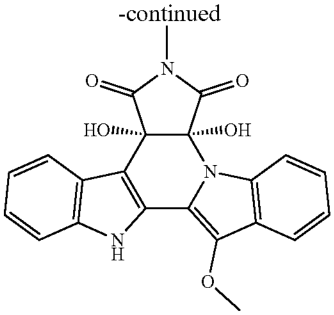

Cladoniamide C;

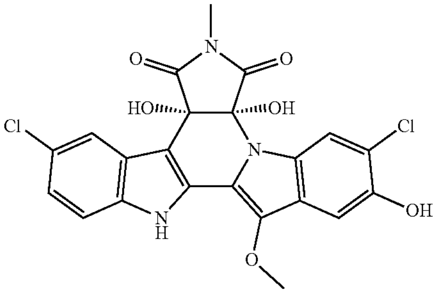

Lazarimide A;

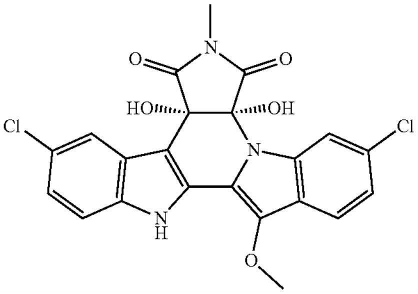

Lazarimide B;

BE-54017

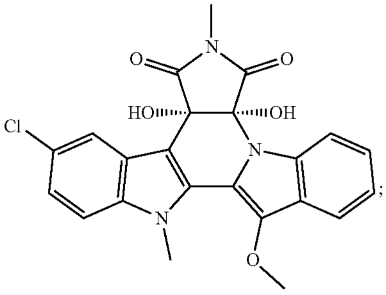

; or

BE-54017'5

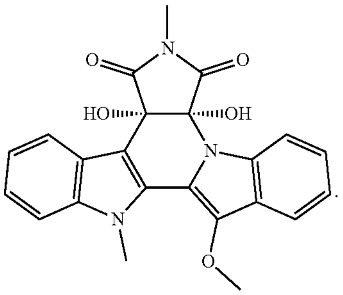

A further embodiment of the present disclosure provides a biosynthetic method for producing a compound of Formula I(a) comprising cultivating a bacterium in a culture medium so to cause accumulation of said compound of Formula I(a) in said culture medium, and optionally isolating said compound of Formula I(a) from said culture medium.

A further embodiment of the present disclosure provides a biosynthetic method for producing a compound of Formula II(a) comprising cultivating a bacterium in a culture medium so to cause accumulation of said compound of Formula II(a) in said culture medium, and optionally isolating said compound of Formula II(a) from said culture medium.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should rather be given the broadest interpretation consistent with the description as a whole.

BRIEF DESCRIPTION OF THE DRAWINGS

The embodiments of the disclosure will now be described in greater detail with reference to the attached drawings, in which.

DETAILED DESCRIPTION

I. Definitions

Figure 1:
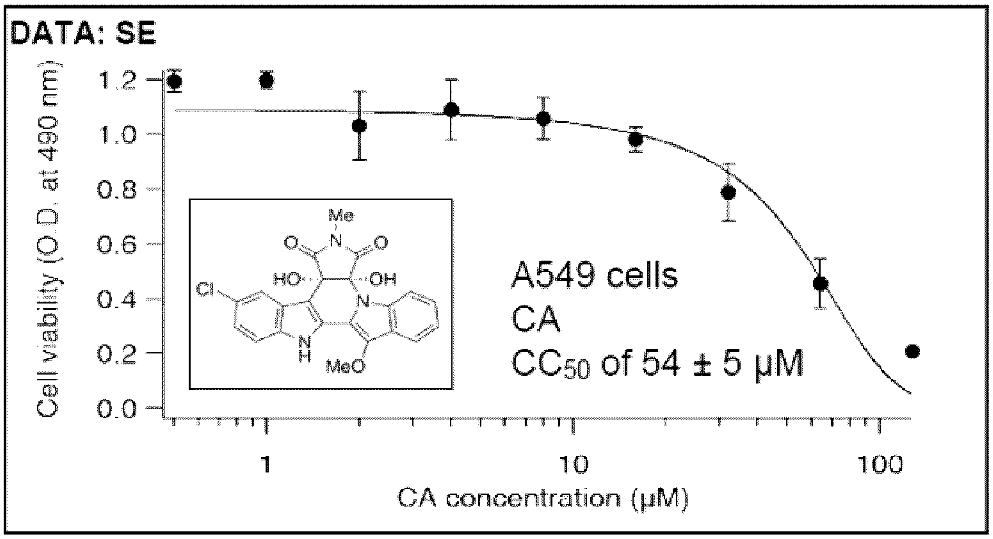
FIG. 1 is a plot to determine cytotoxicity concentration 50% ($CC_{50}$) of cladoniamide A (CA) in A549 cells. Error bars represent SD among two biological replicates.

Unless otherwise indicated, the definitions and embodiments described in this and other sections are intended to be applicable to all embodiments and aspects of the disclosure herein described for which they would be understood to be suitable by a person skilled in the art.

Terms of degree such as "about" and "approximately" as used herein mean a reasonable amount of deviation of the modified term such that the end result is not significantly changed. These terms of degree should be construed as including a deviation of at least ±5% of the modified term if this deviation would not negate the meaning of the term it modifies.

The term "and/or" as used herein means that the listed items are present, or used, individually or in combination. In effect, this term means that "at least one of" or "one or more" of the listed items is present or used.

Numeric ranges are inclusive of the numbers defining the range.

As used in this disclosure, the singular forms "a", "an" and "the" include plural references unless the content clearly dictates otherwise.

As used herein, the words "comprising" (and any form thereof, such as "comprise" and "comprises"), "having" (and any form thereof, such as "have" and "has"), "including" (and any form thereof, such as "include" and "includes") or "containing" (and any form thereof, such as "contain" and "contains"), are inclusive or open-ended and do not exclude additional, unrecited elements or process/method steps. As used herein, the word "consisting" and its derivatives are intended to be close-ended terms that specify the presence of the stated features, elements, components, groups, integers and/or steps, and also exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of these features, elements, components, groups, integers and/or steps.

The term "suitable" as used herein means that the selection of the particular compound and/or conditions would depend on the specific synthetic manipulation to be performed, and/or the identity of the compound(s) to be transformed, but the selection would be well within the skill of a person skilled in the art. All method steps described herein are to be conducted under conditions sufficient to provide the product shown. A person skilled in the art would understand that all reaction conditions, including, for example, reaction solvent or lack thereof, reaction time, reaction temperature, reaction pressure, reactant ratio and whether or not the reaction should be performed under an anhydrous or inert atmosphere, can be varied to optimize the yield of the desired product and it is within their skill to do so.

The term "halo" as used herein refers to a halogen atom and includes F, Cl, Br and I. In an embodiment of the present disclosure, halo is chloro.

The term "alkyl" as used herein, whether it is used alone or as part of another group, means straight or branched chain, saturated alkyl groups. The number of carbon atoms that are possible in the referenced alkyl group are indicated by the numerical prefix "$C_{n1-n2}$". For example, the term $C_{1-6}$alkyl means an alkyl group having 1, 2, 3, 4, 5 or 6 carbon atoms.

The term "cycloalkyl" as used herein, whether it is used alone or as part of another group, means a mono- or bicyclic, saturated cycloalkyl group. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms. When a cycloalkyl group contains more than one cyclic structure or rings, the cyclic structures may be fused, bridged, spiro connected or linked by a single bond. The term "fused" as used herein in reference to a first cyclic structure being "fused" with a second cyclic structure means the first cyclic structure and the second cyclic structure share at least two adjacent atoms therebetween. The term "bridged" as used herein in reference to a first cyclic structure being "bridged" with a second cyclic structure means the first cyclic structure and the second cyclic structure share at least two non-adjacent atoms therebetween. The term "spiro connected" in reference to a first cyclic structure being "spiro connected" with a second cyclic structure means the first cyclic structure and the second cyclic structure share one atom therebetween.

The term "alkylene" as used herein, whether it is used alone or as part of another group, means a straight or branched chain, bivalent form of an alkane, that is, a saturated carbon chain that links two other groups. The number of carbon atoms that are possible in the referenced alkylene group are indicated by the numerical prefix "$C_{n1-n2}$". For example, the term $C_{1-6}$alkylene means an alkylene group having 1, 2, 3, 4, 5 or 6 carbon atoms.

The terms "aryl" and "aromatic cycle" as used herein, whether used alone or as part of another group, refers to groups that contain at least one aromatic ring. When an aryl group contains more than one aromatic ring the terms "aryl" and "aromatic cycle" as used herein include condensed aromatic systems. In an embodiment, the aryl group contains from 6, 9, 10 or 14 atoms, such as phenyl, naphthyl, indanyl or anthracenyl. The number of carbon atoms that are possible in the referenced aryl group are indicated by the numerical prefix "$C_{n1-n2}$". For example, the term $C_{6-10}$aryl means an aryl group having 6, 7, 8, 9 or 10 carbon atoms.

The terms "heteroaryl" and "aromatic heterocycle" as used herein, whether used alone or as part of another group, refers to an aromatic, ring-containing group having one or more multivalent heteroatoms (for example, heteroatoms independently selected from N, O and S), as a part of the ring structure. In an embodiment of the present disclosure, the heteroaryl includes at least 5 and up to 20 atoms in the ring(s). Heteroaryl groups may contain more than one ring.

The term "carbocyclic" as used herein in reference to a "carbocyclic ring", refers to a group containing at least one ring in which all of the atoms of the ring(s) are carbon atoms.

The term "heterocyclic" as used herein in reference to a "heterocyclic ring", refers to a group containing at least one ring, in which at least one ring in the group has one or more multivalent heteroatoms (for example, heteroatoms independently selected from N, O and S), as a part of the ring structure. In an embodiment of the present disclosure, the heterocyclic ring includes at least 5 and up to 20 atoms in the ring(s).

The term "haloalkyl" as used herein refers to an alkyl group wherein one or more, including all of the available hydrogen atoms are replaced by a halogen atom. The number of carbon atoms that are possible in the referenced haloalkyl group are indicated by the numerical prefix "$C_{n1-n2}$". For example, the term $C_{1-6}$haloalkyl means a haloalkyl group having 1, 2, 3, 4, 5 or 6 carbon atoms. In an embodiment, the halogen is a fluorine, in which case the haloalkyl is optionally referred to herein as a "fluoroalkyl" group. It is an embodiment that all of the hydrogen atoms are replaced by fluorine atoms.

The term "substituted" as used herein in reference to a group refers to such a group wherein one or more, including all of the available hydrogen atoms are replaced by a substituent. In an embodiment, the substituents are selected from H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein R' and R" are each independently H, alkyl or alkylene-aryl.

The term "cladoniamide A" as used herein refers to a compound with an IUPAC name computed by LexiChem 2.6.6 of "(11S,15R)-7-chloro-11,15-dihydroxy-23-methoxy-13-methyl-3,13,16-triazahexacyclo[14.7.0.0$^{2,10}$.0$^{4,9}$.0$^{11,15}$.0$^{17,22}$]tricosa-1(23),2(10),4(9),5,7,17,19,21-octaene-12,14-dione" and having the following chemical structure:

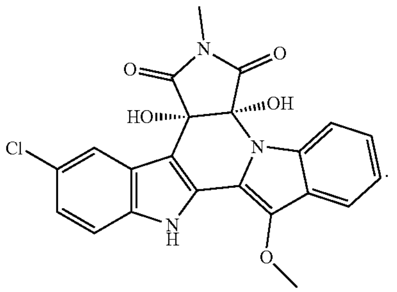 [SMILES: COc1c2n(c3ccccc13)[C@]1(O)C(=O)N(C)C(=O)[C@]1(O)c1c-2[nH]c2ccc(Cl)cc12]

The term "cladoniamide C" as used herein refers to a compound with an IUPAC name computed by LexiChem 2.6.6 of "(11S,15R)-11,15-dihydroxy-23-methoxy-13-methyl-3,13,16-triazahexacyclo[14.7.0.0$^{2,10}$.0$^{4,9}$.0$^{11,15}$.0$^{17,22}$]tricosa-1(23),2(10),4,6,8,17,19,21-octaene-12,14-dione" and having the following chemical structure:

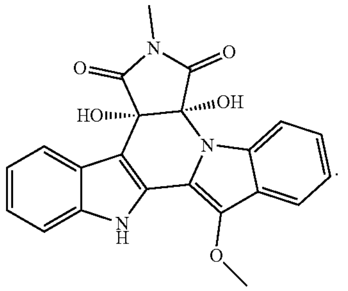 [SMILES: COc1c2n(c3ccccc13)[C@]1(O)C(=O)N(C)C(=O)[C@]1(O)c1c-2[nH]c2ccccc12]

The term "cladoniamide D" as used herein refers to a compound with an IUPAC name computed by LexiChem 2.6.6 of "(12R)-7-chloro-12-hydroxy-20-methoxy-N-methyl-11-oxo-3,13-diazapentacyclo[11.7.0.0$^{2,10}$.0$^{4,9}$.0$^{14,19}$]icosa-1(20),2(10),4(9),5,7,14,16,18-octaene-12-carboxamide" and having the following chemical structure:

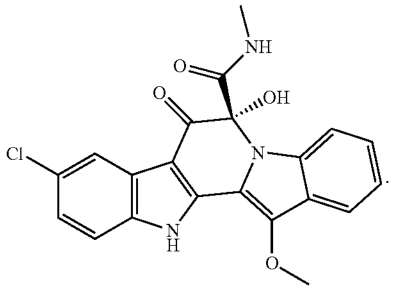 [SMILES: CNC(=O)[C@]1(O)C(=O)c2c([nH]c3ccc(Cl)cc23)-c2c(OC)c3ccccc3n21]

The term "cladoniamide E" as used herein refers to a compound with an IUPAC name computed by LexiChem 2.6.6 of "(12R)-7,17-dichloro-12-hydroxy-20-methoxy-N-methyl-11-oxo-3,13-diazapentacyclo[11.7.0.$0^{2,10}$.$0^{4,9}$.$0^{14,19}$]icosa-1(20),2(10),4(9),5,7,14(19),15,17-octaene-12-carboxamide" and having the following chemical structure:

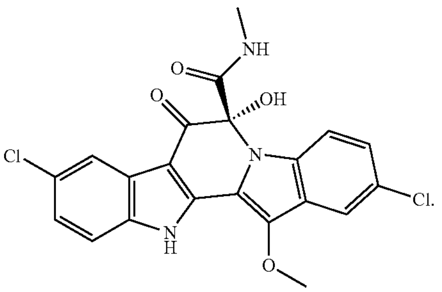 [SMILES: CNC(=O)[C@]1(O)C(=O)c2c([nH]c3ccc(Cl)cc23)-c2c(OC)c3cc(Cl)ccc3n21]

The term "cladoniamide F" as used herein refers to a compound with an IUPAC name computed by LexiChem 2.6.6 of "(11R)-7-chloro-11-hydroxy-20-methoxy-N-methyl-12-oxo-3,13-diazapentacyclo[11.7.0.$0^{2,10}$.$0^{4,9}$.$0^{14,19}$]icosa-1(20),2(10),4(9),5,7,14,16,18-octaene-11-carboxamide" and having the following chemical structure:

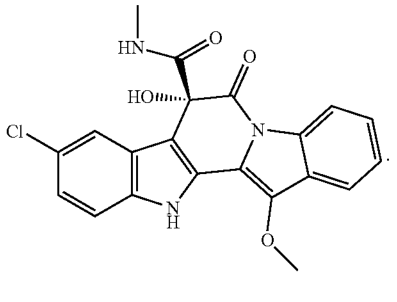 [SMILES: CNC(=O)[C@@]1(O)C(=O)n2c(c(OC)c3ccccc32)-c2[nH]c3ccc(Cl)cc3c21]

In embodiments of the disclosure, the compounds described herein have at least one asymmetric center. Where compounds possess more than one asymmetric center, they may exist as diastereomers. It is to be understood that all such isomers and mixtures thereof in any proportion are encompassed within the scope of the present disclosure. It is to be further understood that while the stereochemistry of the compounds may be as shown in any given compound listed herein, such compounds may also contain certain amounts (e.g. less than 20%, optionally less than 10%, optionally less than 5%, optionally less than 3%) of the corresponding compound having alternate stereochemistry.

The term "subject" as used herein includes all members of the animal kingdom including mammals and birds (class Aves), and optionally refers to humans.

The term "pharmaceutically acceptable" means compatible with the treatment of subjects, for example, mammals (such as humans) or birds.

The term "pharmaceutically acceptable salt" as used herein means an acid addition salt or a base addition salt that is compatible with the treatment of subjects.

An "acid addition salt that is compatible with the treatment of subjects" is any non-toxic inorganic or organic salt of any basic compound. Basic compounds that form an acid addition salt include, for example, compounds comprising an amine group susceptible to protonation. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that may form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Such salts may exist in a hydrated, solvated or substantially anhydrous form. The selection of a suitable salt can be made by a person skilled in the art. The formation of a desired acid addition salt is, for example, achieved using standard techniques. For example, in an embodiment of the present disclosure, the neutral compound is treated with the desired acid in a suitable solvent and the salt which is thereby formed then isolated by filtration, extraction and/or any other suitable method.

A "base addition salt that is compatible with the treatment of subjects" is any non-toxic inorganic or organic salt of any acidic compound. Acidic compounds that form a base addition salt include, for example, compounds comprising a carboxylic acid group. Inorganic bases that may form suitable salts include, without limitation, lithium, sodium, potassium, calcium, magnesium or barium hydroxide. Organic bases that may form suitable salts include, without limitation, aliphatic, alicyclic or aromatic organic amines such as methylamine, trimethylamine and picoline or ammonia. The selection of a suitable salt can be made by a person skilled in the art. The formation of a desired base addition salt is, for example, achieved using standard techniques. For example, in an embodiment of the present disclosure, the neutral compound is treated with the desired base in a suitable solvent and the salt which is thereby formed then isolated by filtration, extraction and/or any other suitable method.

The terms "to treat", "treating" and "treatment" and the like as used herein and as is well understood in the art, means an approach for obtaining beneficial or desired results, including clinical results. For example, in the context of treating a viral infection, beneficial or desired clinical results include, but are not limited to alleviation or amelioration of one or more symptoms of the viral infection, diminishment of the extent of the viral infection, stabilized (i.e., not worsening) of the viral infection, delay or slowing of the progression of the viral infection, amelioration or palliation of the disease state of the viral infection, diminishment of the reoccurrence of the viral infection, and/or remission (whether partial or total) of the viral infection, whether detectable or undetectable. "To treat", "treating" and "treatment" and the like as used herein also include prophylactic treatment.

The compounds of the present disclosure are, for example, administered to the subject or used in an "effective amount".

As used herein, the term "effective amount" and the like means an amount effective, at dosages and for periods of time necessary to achieve a desired result. For example, in the context of treating a viral infection, an effective amount of a compound administered or used is an amount that, for example, reduces the viral infection compared to the viral infection without administration or use of the compound. Effective amounts may vary according to factors such as the disease state, age, sex, weight and/or species of the subject. The amount of a given compound that will correspond to such an amount will vary depending upon various factors, such as the given compound, the pharmaceutical formulation, the route of administration or use, the type of viral infection being treated, the identity of the subject being treated, and the like, but can nevertheless be routinely determined by one skilled in the art.

II. Methods of Treatment and Uses

Cladoniamide A produced by actinomycete *Streptomyces* unicialis is active against coronavirus and flavivirus. While *S. unicialis* also produces other cladoniamides, such as e.g. cladoniamide D, cladoniamide D possessed no activity against DENV and ZIKV. Similar results were also found for SARS-CoV-2. Cladoniamide E and cladoniamide F similarly showed no activity against ZIKV. Cladoniamide A was found to be a highly effective antiviral against the UK strain of SARS-CoV-2 (202012/01), with an $ED_{50}$ of about 800 pM. Cladoniamide A and cladoniamide C both showed anti-ZIKV activity in brain organoids infected with ZIKV.

Accordingly, the present disclosure includes a use of a compound of the Formula I or a pharmaceutically acceptable salt thereof for treatment of a viral infection in a subject in need thereof:

I

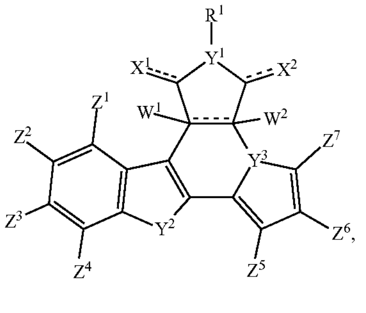

wherein

- each ⎓ independently represents a single or double bond;
- $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", $NR'SO_2R"$, $CO_2R'$, COR', $CS_2R'$, CSR', CONR'R", NR'COR", CSNR'R", NR'CSR", OR', SR', $SO_2R'$, SOR', $SO_2NR'R"$, CN or haloalkyl, wherein the alkyl, cycloalkyl, alkylene-aryl, aryl and heteroaryl are optionally substituted; or
- one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", $NR'SO_2R"$, $CO_2R'$, COR', $CS_2R'$, CSR', CONR'R", NR'COR", CSNR'R", NR'CSR", OR', SR', $SO_2R'$, SOR', $SO_2NR'R"$, CN or haloalkyl, wherein the alkyl, cycloalkyl, alkylene-aryl, aryl and heteroaryl are optionally substituted;
- $X^1$ and $X^2$ are each independently O, H or OR';
- $Y^1$ is N or CR';
- $Y^2$ is NR', S, O or CR';
- $Y^3$ is N or CR';
- $W^1$ and $W^2$ are both absent or are each independently H, OR', NR' or SR';
- $R^1$ is H or an optionally substituted alkyl; and
- R' and R" are each independently H or an optionally substituted alkyl or alkylene-aryl.

The present disclosure also includes a use of a compound of the Formula I or a pharmaceutically acceptable salt thereof for preparation of a medicament for treatment of a viral infection in a subject in need thereof:

I

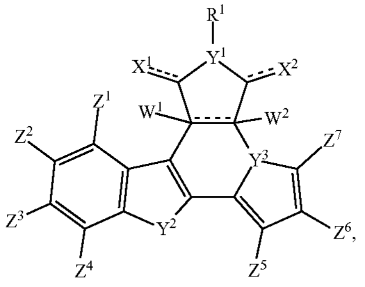

wherein

- each ⎓ independently represents a single or double bond;
- $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", $NR'SO_2R"$, $CO_2R'$, COR', $CS_2R'$, CSR', CONR'R", NR'COR", CSNR'R", NR'CSR", OR', SR', $SO_2R'$, SOR', $SO_2NR'R"$, CN or haloalkyl, wherein the alkyl, cycloalkyl, alkylene-aryl, aryl and heteroaryl are optionally substituted; or
- one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", $NR'SO_2R"$, $CO_2R'$, COR', $CS_2R'$, CSR', CONR'R", NR'COR", CSNR'R", NR'CSR", OR', SR', $SO_2R'$, SOR', $SO_2NR'R"$, CN or haloalkyl, wherein the alkyl, cycloalkyl, alkylene-aryl, aryl and heteroaryl are optionally substituted;
- $X^1$ and $X^2$ are each independently O, H or OR';
- $Y^1$ is N or CR';
- $Y^2$ is NR', S, O or CR';
- $Y^3$ is N or CR';
- $W^1$ and $W^2$ are both absent or are each independently H, OR', NR' or SR';
- $R^1$ is H or an optionally substituted alkyl; and
- R' and R" are each independently H or an optionally substituted alkyl or alkylene-aryl.

The present disclosure also includes a compound of the Formula I or a pharmaceutically acceptable salt thereof for use to treat a viral infection in a subject in need thereof.

I

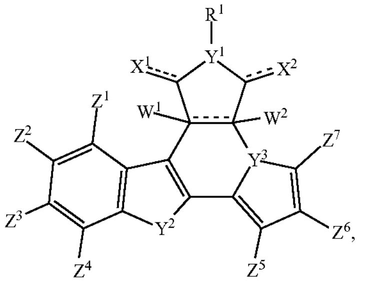

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

The present disclosure also includes a method of treating a viral infection in a subject in need thereof, the method comprising administering a compound of the Formula I or a pharmaceutically acceptable salt thereof to the subject:

I

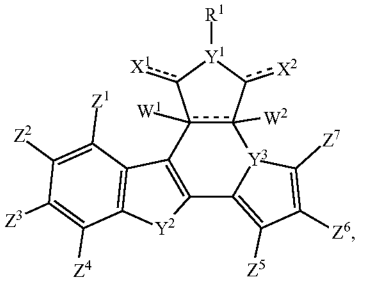

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

A person skilled in the art would readily appreciate in which embodiments ⎓ represents a single bond and in which embodiments ⎓ represents a double bond. For example, the skilled person would readily understand that when $X^1$ and/or $X^2$ is 0, the bond attaching the $X^1$ and/or the $X^2$ to the remainder of the Formula I is a double bond whereas when $X^1$ and/or $X^2$ is H or OR' the bond attaching the $X^1$ and/or the $X^2$ to the remainder of the Formula I is a single bond. Similarly, the skilled person would appreciate that when $W^1$ and $W^2$ are both absent, the bond connecting the carbons to which $W^1$ and $W^2$ are attached is a double bond whereas when $W^1$ and $W^2$ are each independently H, OR', NR' or SR' the bond connecting the carbons to which $W^1$ and $W^2$ are attached is a single bond.

In an embodiment, $X^1$ and $X^2$ are each independently O, H or OR', wherein OR' is H or $C_{1-6}$alkyl. In another embodiment, $X^1$ and $X^2$ are each independently OR', wherein OR' is H or $C_{1-6}$alkyl. In a further embodiment, $X^1$ and $X^2$ are both OH.

In an embodiment, $Y^1$ is N.

In an embodiment, $Y^2$ is NR', S, O or CR', wherein each R' is independently H or $C_{1-6}$alkyl. In another embodiment of the present disclosure, $Y^2$ is NR', wherein R' is H or $C_{1-6}$alkyl. In a further embodiment, $Y^2$ is NR', wherein R' is H.

In an embodiment, $Y^3$ is N.

In an embodiment, $W^1$ and $W^2$ are absent. In another embodiment, $W^1$ and $W^2$ are each independently H, OR', NR' or SR'. In a further embodiment, $W^1$ and $W^2$ are each OR', wherein each R' is independently H or $C_{1-6}$alkyl. In another embodiment, both $W^1$ and $W^2$ are OH.

In an embodiment, $R^1$ is H or unsubstituted $C_{1-6}$alkyl. In another embodiment, $R^1$ is $C_{1-4}$alkyl. In a further embodiment, $R^1$ is methyl.

In an embodiment, $Z^6$ and $Z^7$ together form a substituted aromatic ring or an unsubstituted aromatic ring. In an embodiment, $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$.

In an embodiment, $Z^5$ is OR', wherein R' is alkyl. In another embodiment, $Z^5$ is OR', wherein R' is $C_{1-6}$alkyl. In a further embodiment, $Z^5$ is $OCH_3$.

In an embodiment, $Z^1$, $Z^3$ and $Z^4$ are all H.

In an embodiment, $Z^2$ is halo or H. In another embodiment, $Z^2$ is halo. In another embodiment, $Z^2$ is chloro. In a further embodiment, $Z^2$ is H.

In an embodiment, $Z^6$ and $Z^7$ together form a 6-membered aromatic ring. In another embodiment, $Z^6$ and $Z^7$ together form an unsubstituted, 6-membered aromatic ring.

In an embodiment, R' and R" are each independently H or an optionally substituted $C_{1-10}$alkyl or $C_{1-10}$alkylene-aryl. In another embodiment, R' and R" are each independently H or an optionally substituted $C_{1-6}$alkyl or $C_{1-6}$alkylene-$C_{6-10}$aryl. In another embodiment, R' is H. In another embodiment, R' is alkyl. In another embodiment, R' is $C_{1-10}$alkyl. In a further embodiment, R' is $C_{1-6}$alkyl. In another embodiment, R' is $C_{1-4}$alkyl. In an embodiment, R' is alkylene-aryl. In another embodiment, R' is $C_{1-10}$alkylene-aryl. In a further embodiment, R' is $C_{1-6}$alkylene$C_{6-10}$aryl. In another embodiment, R" is H. In another embodiment, R" is alkyl. In another embodiment, R" is $C_{1-10}$alkyl. In a further embodiment, R" is $C_{1-6}$alkyl. In another embodiment, R" is $C_{1-4}$alkyl. In an embodiment, R" is alkylene-aryl. In another embodiment, R" is $C_{1-10}$alkylene-aryl. In a further embodiment, R" is $C_{1-6}$alkylene$C_{6-10}$aryl.

In an embodiment, the compound is a compound of Formula I(a):

I(a)

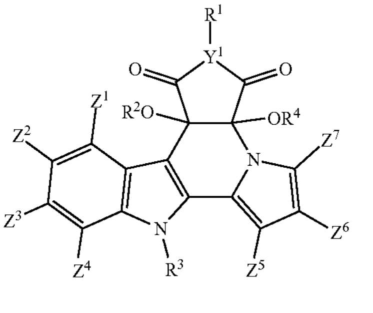

wherein $Z^1$, $Z^2$, $Z^3$, $Z^4$, $Z^5$, $Z^6$, and $Z^7$, are each independently H, halo, optionally substituted alkyl, aryl, heteroaryl, $NO_2$, NR'R", NR'$SO_2$R", CONR'R", NR'COR", OR', SR', CN, or $CF_3$; or $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$;

$R^1$, $R^2$, $R^3$, and $R^4$ are each independently H or an optionally substituted alkyl; and R' and R" are each independently H, or an optionally substituted alkyl.

In an embodiment, $R^1$ is H or unsubstituted $C_{1-6}$alkyl. In another embodiment, $R^1$ is $C_{1-4}$alkyl. In a further embodiment, $R^1$ is methyl.

In an embodiment, $R^2$ and $R^4$ are each independently H or $C_{1-6}$alkyl. In another embodiment, $R^2$ and $R^4$ are both H.

In an embodiment, $R^3$ is H or $C_{1-6}$alkyl. In another embodiment, $R^3$ is H.

In an embodiment, $Z^6$ and $Z^7$ together form a substituted aromatic ring or an unsubstituted aromatic ring. In an embodiment, $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$.

In an embodiment, $Z^5$ is OR', wherein R' is alkyl. In another embodiment, $Z^5$ is OR', wherein R' is $C_{1-6}$alkyl. In a further embodiment, $Z^5$ is $OCH_3$.

In an embodiment, $Z^1$, $Z^3$ and $Z^4$ are all H.

In an embodiment, $Z^2$ is halo or H. In another embodiment, $Z^2$ is halo. In another embodiment, $Z^2$ is chloro. In a further embodiment, $Z^2$ is H.

In an embodiment, $Z^6$ and $Z^7$ together form a 6-membered aromatic ring. In another embodiment, $Z^6$ and $Z^7$ together form an unsubstituted, 6-membered aromatic ring.

In an embodiment, R' and R" are each independently H or an optionally substituted $C_{1-10}$alkyl or $C_{1-10}$alkylene-aryl. In another embodiment, R' and R" are each independently H or an optionally substituted $C_{1-6}$alkyl or $C_{1-6}$alkylene-$C_{6-10}$aryl. In another embodiment, R' is H. In another embodiment, R' is alkyl. In another embodiment, R' is $C_{1-10}$alkyl. In a further embodiment, R' is $C_{1-6}$alkyl. In another embodiment, R' is $C_{1-4}$alkyl. In an embodiment, R' is alkylene-aryl. In another embodiment, R' is $C_{1-10}$alkylene-aryl. In a further embodiment, R' is $C_{1-6}$alkylene$C_{6-10}$aryl. In another embodiment, R" is H. In another embodiment, R" is alkyl. In another embodiment, R" is $C_{1-10}$alkyl. In a further embodiment, R" is $C_{1-6}$alkyl. In another embodiment, R" is $C_{1-4}$alkyl. In an embodiment, R" is alkylene-aryl. In another embodiment, R" is $C_{1-10}$alkylene-aryl. In a further embodiment, R" is $C_{1-6}$alkylene$C_{6-10}$aryl.

In an embodiment, the compound is a compound of Formula III:

III

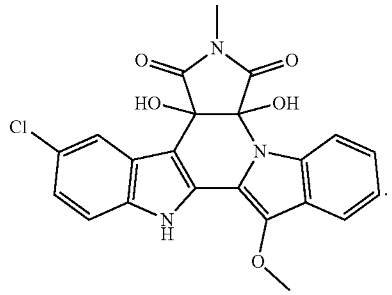

In an embodiment, the compound is cladoniamide A, ent-cladoniamide A or mixtures thereof. In another embodiment, the compound is cladoniamide A. In a further embodiment, the compound is ent-cladoniamide A. In another embodiment, the compound is a mixture of cladoniamide A and ent-cladoniamide A.

In an embodiment, the compound is cladoniamide C.

In an embodiment, the compound or the pharmaceutically acceptable salt thereof is the compound. In another embodiment, the compound or the pharmaceutically acceptable salt thereof is the pharmaceutically acceptable salt of the compound.

In an embodiment, the viral infection is mosquito-borne. In an embodiment, the viral infection is a co-infection of two or more viruses. In an embodiment, the viral infection is caused by one or more coronavirus, flavivirus and/or influenza virus. In an embodiment, the viral infection is caused by one or more coronavirus and/or flavivirus. In another embodiment, the viral infection is caused by one or more coronavirus. In an embodiment, the coronavirus is one or more of severe acute respiratory syndrome (SARS) coronavirus-1 (SARS-CoV-1), SARS coronavirus-2 (SARS-CoV-2), Middle East respiratory syndrome (MERS) coronavirus (MERS-CoV) and human coronavirus 229E (HCoV-229E). In another embodiment, the coronavirus is severe acute respiratory syndrome (SARS) coronavirus-1 (SARS-CoV-1). In another embodiment, the coronavirus is SARS coronavirus-2 (SARS-CoV-2). In a further embodiment, the SARS-CoV-2 is SARS-CoV-2 South Africa (501Y.V2), SARS-CoV-2 UK (VOC 202012/01) or SARS-CoV-2 Nigeria. In an embodiment, the SARS-CoV-2 is SARS-CoV-2 South Africa (501Y.V2). In another embodiment, the SARS-CoV-2 is SARS-CoV-2 UK (VOC 202012/01). In a further embodiment, the SARS-CoV-2 is SARS-CoV-2 Nigeria. In another embodiment, the coronavirus is Middle East respiratory syndrome (MERS) coronavirus (MERS-CoV). In another embodiment, the coronavirus is human coronavirus 229E (HCoV-229E). In an embodiment, the viral infection is caused by one or more flavivirus. In another embodiment, the flavivirus is one or more of dengue virus (DENV), West Nile virus (WNV), Zika virus (ZIKV), Powassan virus (POWV), Japanese encephalitis virus (JEV) and yellow fever virus (YFV). In another embodiment, the flavivirus is one or more of West Nile virus (WNV), Powassan virus (POWV), Japanese encephalitis virus (JEV) and yellow fever virus (YFV). In an embodiment, the flavivirus is dengue virus (DENV). In an embodiment, the DENV is DENV-2, DENV-3, DENV-4 or a combination thereof. In another embodiment, the DENV is DENV-2. In another embodiment, the DENV is DENV-3. In another embodiment, the DENV is DENV-4. In another embodiment, the flavivirus is West Nile virus (WNV). In a further embodiment, the flavivirus is Zika virus (ZIKV). In another embodiment, the flavivirus is Powassan virus (POWV). In another embodiment, the flavivirus is Japanese encephalitis virus (JEV). In an embodiment, the flavivirus is yellow fever virus (YFV). In another embodiment, the viral infection is caused by one or more influenza virus. In an embodiment, the influenza virus is one or more of H1N1 influenza A virus, an H5 avian influenza A virus and an H7 avian influenza A virus. In another embodiment, the influenza virus is H1N1 influenza A virus. In another embodiment, the influenza virus is an H5 avian influenza A virus. In another embodiment, the influenza virus is an H7 avian influenza A virus.

In an embodiment, the subject is a human.

The present disclosure also includes a use of a compound of Formula I or a pharmaceutically acceptable salt thereof for inhibiting vacuolar-$H^+$ATPase (V-ATPase):

I

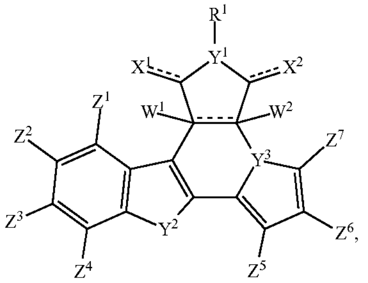

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

The present disclosure also includes a compound of Formula I or a pharmaceutically acceptable salt thereof for use to inhibit vacuolar-$H^+$ATPase (V-ATPase):

I

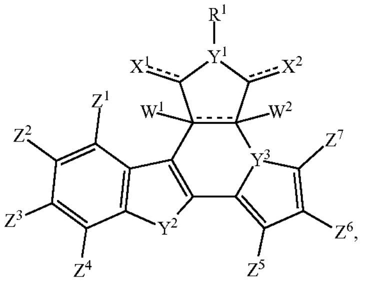

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

The present disclosure also includes a method of inhibiting vacuolar-$H^+$ATPase (V-ATPase) comprising contacting the V-ATPase with a compound of Formula I or a pharmaceutically acceptable salt thereof:

I

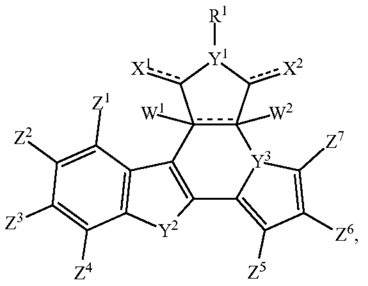

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

A person skilled in the art would readily appreciate in which embodiments ⎓ represents a single bond and in which embodiments ⎓ represents a double bond. For example, the skilled person would readily understand that when $X^1$ and/or $X^2$ is 0, the bond attaching the $X^1$ and/or the $X^2$ to the remainder of the Formula I is a double bond whereas when $X^1$ and/or $X^2$ is H or OR' the bond attaching the $X^1$ and/or the $X^2$ to the remainder of the Formula I is a single bond. Similarly, the skilled person would appreciate that when $W^1$ and $W^2$ are both absent, the bond connecting the carbons to which $W^1$ and $W^2$ are attached is a double bond whereas when $W^1$ and $W^2$ are each independently H, OR', NR' or SR' the bond connecting the carbons to which $W^1$ and $W^2$ are attached is a single bond.

In an embodiment, $X^1$ and $X^2$ are each independently O, H or OR', wherein OR' is H or $C_{1-6}$alkyl. In another embodiment, $X^1$ and $X^2$ are each independently OR', wherein OR' is H or $C_{1-6}$alkyl. In a further embodiment, $X^1$ and $X^2$ are both OH.

In an embodiment, $Y^1$ is N.

In an embodiment, $Y^2$ is NR', S, O or CR', wherein each R' is independently H or $C_{1-6}$alkyl. In another embodiment of the present disclosure, $Y^2$ is NR', wherein R' is H or $C_{1-6}$alkyl. In a further embodiment, $Y^2$ is NR', wherein R' is H.

In an embodiment, $Y^3$ is N.

In an embodiment, $W^1$ and $W^2$ are absent. In another embodiment, $W^1$ and $W^2$ are each independently H, OR', NR' or SR'. In a further embodiment, $W^1$ and $W^2$ are each OR', wherein each R' is independently H or $C_{1-6}$alkyl. In another embodiment, both $W^1$ and $W^2$ are OH.

In an embodiment, $R^1$ is H or unsubstituted $C_{1-6}$alkyl. In another embodiment, $R^1$ is $C_{1-4}$alkyl. In a further embodiment, $R^1$ is methyl.

In an embodiment, $Z^6$ and $Z^7$ together form a substituted aromatic ring or an unsubstituted aromatic ring. In an embodiment, $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$.

In an embodiment, $Z^5$ is OR', wherein R' is alkyl. In another embodiment, $Z^5$ is OR', wherein R' is $C_{1-6}$alkyl. In a further embodiment, $Z^5$ is $OCH_3$.

In an embodiment, $Z^1$, $Z^3$ and $Z^4$ are all H.

In an embodiment, $Z^2$ is halo or H. In another embodiment, $Z^2$ is halo. In another embodiment, $Z^2$ is chloro. In a further embodiment, $Z^2$ is H.

In an embodiment, $Z^6$ and $Z^7$ together form a 6-membered aromatic ring. In another embodiment, $Z^6$ and $Z^7$ together form an unsubstituted, 6-membered aromatic ring.

In an embodiment, R' and R" are each independently H or an optionally substituted $C_{1-10}$alkyl or $C_{1-10}$alkylene-aryl. In another embodiment, R' and R" are each independently H or an optionally substituted $C_{1-6}$alkyl or $C_{1-6}$alkylene-$C_{6-10}$ aryl. In another embodiment, R' is H. In another embodiment, R' is alkyl. In another embodiment, R' is $C_{1-10}$alkyl. In a further embodiment, R' is $C_{1-6}$alkyl. In another embodiment, R' is $C_{1-4}$alkyl. In an embodiment, R' is alkylene-aryl. In another embodiment, R' is $C_{1-10}$alkylene-aryl. In a further embodiment, R' is $C_{1-6}$alkylene$C_{6-10}$aryl. In another embodiment, R" is H. In another embodiment, R" is alkyl. In another embodiment, R" is $C_{1-10}$alkyl. In a further embodiment, R" is $C_{1-6}$alkyl. In another embodiment, R" is $C_{1-4}$alkyl. In an embodiment, R" is alkylene-aryl. In another embodiment, R" is $C_{1-10}$alkylene-aryl. In a further embodiment, R" is $C_{1-6}$alkylene$C_{6-10}$aryl.

In an embodiment, the compound is a compound of Formula I(a):

I(a)

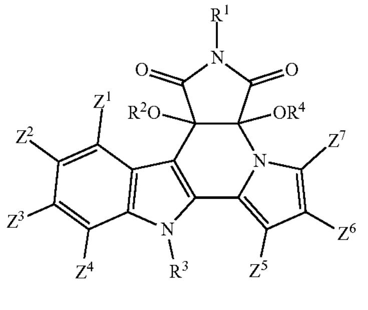

wherein

- $Z^1$, $Z^2$, $Z^3$, $Z^4$, $Z^5$, $Z^6$, and $Z^7$, are each independently H, halo, optionally substituted alkyl, aryl, heteroaryl, $NO_2$, NR'R", NR'$SO_2$R", CONR'R", NR'COR", OR', SR', CN, or $CF_3$; or
- $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$;
- $R^1$, $R^2$, $R^3$, and $R^4$ are each independently H or an optionally substituted alkyl; and
- R' and R" are each independently H, or an optionally substituted alkyl.

In an embodiment, $R^1$ is H or unsubstituted $C_{1-6}$alkyl. In another embodiment, $R^1$ is $C_{1-4}$alkyl. In a further embodiment, $R^1$ is methyl.

In an embodiment, $R^2$ and $R^4$ are each independently H or $C_{1-6}$alkyl. In another embodiment, $R^2$ and $R^4$ are both H.

In an embodiment, $R^3$ is H or $C_{1-6}$alkyl. In another embodiment, $R^3$ is H.

In an embodiment, $Z^6$ and $Z^7$ together form a substituted aromatic ring or an unsubstituted aromatic ring. In an embodiment, $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$.

In an embodiment, $Z^5$ is OR', wherein R' is alkyl. In another embodiment, $Z^5$ is OR', wherein R' is $C_{1-6}$alkyl. In a further embodiment, $Z^5$ is $OCH_3$.

In an embodiment, $Z^1$, $Z^3$ and $Z^4$ are all H.

In an embodiment, $Z^2$ is halo or H. In another embodiment, $Z^2$ is halo. In another embodiment, $Z^2$ is chloro. In a further embodiment, $Z^2$ is H.

In an embodiment, $Z^6$ and $Z^7$ together form a 6-membered aromatic ring. In another embodiment, $Z^6$ and $Z^7$ together form an unsubstituted, 6-membered aromatic ring.

In an embodiment, R' and R" are each independently H or an optionally substituted $C_{1-10}$alkyl or $C_{1-10}$alkylene-aryl. In another embodiment, R' and R" are each independently H or an optionally substituted $C_{1-6}$alkyl or $C_{1-6}$alkylene-$C_{6-10}$ aryl. In another embodiment, R' is H. In another embodiment, R' is alkyl. In another embodiment, R' is $C_{1-10}$alkyl. In a further embodiment, R' is $C_{1-6}$alkyl. In another embodiment, R' is $C_{1-4}$alkyl. In an embodiment, R' is alkylene-aryl. In another embodiment, R' is $C_{1-10}$alkylene-aryl. In a further embodiment, R' is $C_{1-6}$alkylene$C_{6-10}$aryl. In another embodiment, R" is H. In another embodiment, R" is alkyl. In another embodiment, R" is $C_{1-10}$alkyl. In a further embodiment, R" is $C_{1-6}$alkyl. In another embodiment, R" is $C_{1-4}$alkyl. In an embodiment, R" is alkylene-aryl. In another embodiment, R" is $C_{1-10}$alkylene-aryl. In a further embodiment, R" is $C_{1-6}$alkylene$C_{6-10}$aryl.

In an embodiment, the compound is a compound of Formula III:

III

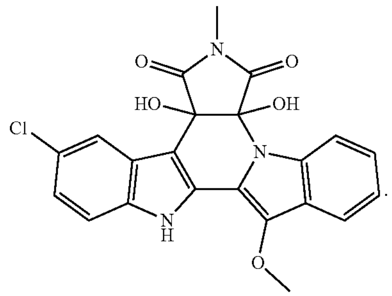

In an embodiment, the compound is cladoniamide A, ent-cladoniamide A or mixtures thereof. In another embodiment, the compound is cladoniamide A. In a further embodiment, the compound is ent-cladoniamide A. In another embodiment, the compound is a mixture of cladoniamide A and ent-cladoniamide A.

In an embodiment, the compound is cladoniamide C.

In an embodiment, the compound or the pharmaceutically acceptable salt thereof is the compound. In another embodiment, the compound or the pharmaceutically acceptable salt thereof is the pharmaceutically acceptable salt of the compound.

In an embodiment, the inhibition of V-ATPase is in a subject.

In an embodiment, the subject is a human.

In an embodiment, the subject suffers from a viral infection.

In an embodiment, the viral infection is mosquito-borne. In an embodiment, the viral infection is a co-infection of two or more viruses. In an embodiment, the viral infection is caused by one or more coronavirus, flavivirus and/or influenza virus. In an embodiment, the viral infection is caused by one or more coronavirus and/or flavivirus. In another embodiment, the viral infection is caused by one or more coronavirus. In an embodiment, the coronavirus is one or more of severe acute respiratory syndrome (SARS) coronavirus-1 (SARS-CoV-1), SARS coronavirus-2 (SARS-CoV-2), Middle East respiratory syndrome (MERS) coronavirus (MERS-CoV) and human coronavirus 229E (HCoV-229E). In another embodiment, the coronavirus is severe acute respiratory syndrome (SARS) coronavirus-1 (SARS-CoV-1). In another embodiment, the coronavirus is SARS coronavirus-2 (SARS-CoV-2). In a further embodiment, the SARS-CoV-2 is SARS-CoV-2 South Africa (501Y.V2), SARS-CoV-2 UK (VOC 202012/01) or SARS-CoV-2 Nigeria. In an embodiment, the SARS-CoV-2 is SARS-CoV-2 South Africa (501Y.V2). In another embodiment, the SARS-CoV-2 is SARS-CoV-2 UK (VOC 202012/01). In a further embodiment, the SARS-CoV-2 is SARS-CoV-2 Nigeria. In another embodiment, the coronavirus is Middle East respiratory syndrome (MERS) coronavirus (MERS-CoV). In another embodiment, the coronavirus is human coronavirus 229E (HCoV-229E). In an embodiment, the viral infection is caused by one or more flavivirus. In another embodiment, the flavivirus is one or more of dengue virus (DENV), West Nile virus (WNV), Zika virus (ZIKV), Powassan virus (POWV), Japanese encephalitis virus (JEV) and yellow fever virus (YFV). In another embodiment, the flavivirus is one or more of West Nile virus (WNV), Powassan virus (POWV), Japanese encephalitis virus (JEV) and yellow fever virus (YFV). In an embodiment, the flavivirus is dengue virus (DENV). In an embodiment, the DENV is DENV-2, DENV-3, DENV-4 or a combination thereof. In another embodiment, the DENV is DENV-2. In another embodiment, the DENV is DENV-3. In another embodiment, the DENV is DENV-4. In another embodiment, the flavivirus is West Nile virus (WNV). In a further embodiment, the flavivirus is Zika virus (ZIKV). In another embodiment, the flavivirus is Powassan virus (POWV). In another embodiment, the flavivirus is Japanese encephalitis virus (JEV). In an embodiment, the flavivirus is yellow fever virus (YFV). In another embodiment, the viral infection is caused by one or more influenza virus. In an embodiment, the influenza virus is one or more of H1N1 influenza A virus, an H5 avian influenza A virus and an H7 avian influenza A virus. In another embodiment, the influenza virus is H1N1 influenza A virus. In another embodiment, the influenza virus is an H5 avian influenza A virus. In another embodiment, the influenza virus is an H7 avian influenza A virus.

In an embodiment, the compound is administered or used in a pharmaceutical composition comprising the compound and optionally a pharmaceutically acceptable carrier.

The compound can be administered to a subject or used in a variety of forms depending on the selected route of administration or use, as will be understood by those skilled in the art. In an embodiment, the compound is administered to the subject, or used, by oral (including buccal) or parenteral (including intravenous, intraperitoneal, subcutaneous, intramuscular, transepithelial, nasal, intrapulmonary, intrathecal, rectal, topical, patch, pump and transdermal) administration or use and the compound formulated accordingly. For example, the compound is administered or used in an injection, in a spray, in a tablet/caplet, in a powder, topically, in a gel, in drops, by a patch, by an implant, by a slow release pump or by any other suitable method of administration or use, the selection of which can be made by a person skilled in the art.

In an embodiment, the compound is orally administered or used, for example, with an inert diluent or with an assimilable edible carrier, or enclosed in hard- or soft-shell gelatin capsules, or compressed into tablets, or incorporated directly with the food of the diet. In an embodiment, for oral therapeutic administration or use, the compound is incorporated with excipient and administered or used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as molecular sieving type particles, or, a fine hollow permeable fiber bundle, or chopped hollow permeable fibers, agglomerated or held in a fibrous packet. Timed-release compositions can be formulated, e.g. liposomes or those wherein the compound is protected with differentially degradable coatings, such as by microencapsulation, multiple coatings, etc.

In another embodiment, the compound is administered or used parenterally. Solutions of the compound are, for example, prepared in water optionally mixed with a surfactant such as hydroxypropylcellulose. In a further example, dispersions are prepared in glycerol, liquid polyethylene glycols, dimethyl sulfoxide (DMSO) or mixtures thereof with or without alcohol, or in oils. Pharmaceutical forms suitable for injectable administration or use include sterile aqueous solutions or dispersions and sterile powders for the extemporaneous preparation of sterile injectable solutions or dispersions. A person skilled in the art would know how to select and to prepare suitable formulations.

Treatment methods or uses comprise administering to a subject or use of an effective amount of the compound, optionally consisting of a single administration or use, or alternatively comprising a series of administrations or uses. For example, the compound is administered or used at least once a week. However, in another embodiment, the compound is administered to the subject or used from one time per three weeks, or one time per week to once daily for a given treatment or use. In another embodiment, the compound is administered or used 2, 3, 4, 5 or 6 times daily. The length of the treatment period or use depends on a variety of factors, such as the severity and/or type of the viral infection, the age of the subject, the concentration of the compound in a formulation, the activity of the compound and/or a combination thereof. It will also be appreciated that the effective amount of a compound used for the treatment or use may increase or decrease over the course of a particular treatment regime or use. Changes in dosage may result and become apparent by standard diagnostic assays known in the art. In some instances, chronic administration or use is required. For example, the compound is administered or used in an amount and for a duration sufficient to treat the subject.

The compound may be administered or used alone or in combination with other therapeutic agents useful for treating a viral infection. When administered or used in combination with other known therapeutic agents, it is an embodiment that the compound is administered or used contemporaneously with those therapeutic agents. As used herein, the term "contemporaneous" in reference to administration of two substances to a subject or use means providing each of the two substances so that they are both biologically active in the individual at the same time. The exact details of the administration or use will depend on the pharmacokinetics of the two substances in the presence of each other, and can include administering or using the two substances within a few hours of each other, or even administering or using one substance within 24 hours of administration or use of the other, if the pharmacokinetics are suitable. Design of suitable dosing regimens is routine for one skilled in the art. In particular embodiments, two substances will be administered or used substantially simultaneously, i.e., within minutes of each other, or in a single composition that contains both substances. It is a further embodiment that a combination of the two substances is administered to a subject or used in a non-contemporaneous fashion.

The dosage of the compound can vary depending on many factors such as the pharmacodynamic properties of the compound, the mode of administration or use, the age, health and weight of the subject, the type of viral infection, the nature of and/or extent of the symptoms of the viral infection, the frequency of the treatment or use and the type of concurrent treatment or use, if any, and the clearance rate of the compound in the subject. One of skill in the art can determine the appropriate dosage based on the above factors. In an embodiment, the compound is administered or used initially in a suitable dosage that is optionally adjusted as required, depending on the clinical response. As a representative example, oral dosages of the compound will range from less than 1 mg per day to 1000 mg per day for a human adult or an animal. In an embodiment of the present disclosure, the pharmaceutical compositions are formulated for oral administration or use and the compounds are, for example in the form of tablets containing 0.001, 0.01, 0.1, 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. In an embodiment, the compound is administered or used in a single daily dose or the total daily dose may be divided into e.g. two, three or four daily doses.

The present disclosure also includes a use of a compound of Formula I or a pharmaceutically acceptable salt thereof as defined herein to assess activity of a virus (e.g. a virus causing a viral infection as defined herein) against a vacuolar-$H^+$ATPase (V-ATPase).

III. Compounds, Compositions and Methods of Preparation

The present disclosure also includes a compound of Formula I(b):

I(b)

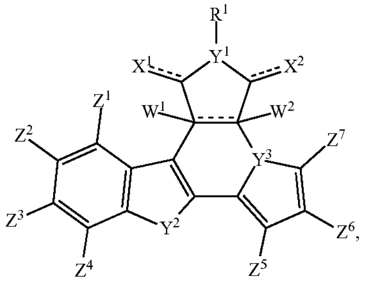

wherein each ⎓ independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", $NR'SO_2R"$, $CO_2R'$, COR', $CS_2R'$, CSR', CONR'R", NR'COR", CSNR'R", NR'CSR", OR', SR', $SO_2R'$, SOR', $SO_2NR'R"$, CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", $NR'SO_2R"$, $CO_2R'$, COR', $CS_2R'$, CSR', CONR'R", NR'COR", CSNR'R", NR'CSR", OR', SR', $SO_2R'$, SOR', $SO_2NR'R"$, CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl, or a pharmaceutically acceptable salt thereof, with the proviso that said compound is not exactly:

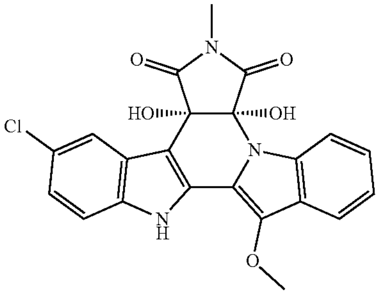

Cladoniamide A;

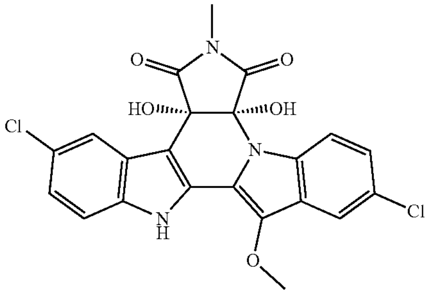

Cladoniamide B;

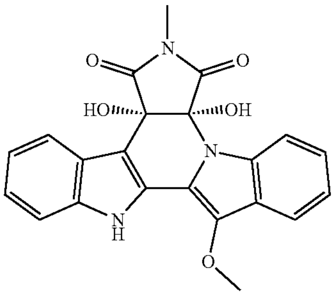

Cladoniamide C;

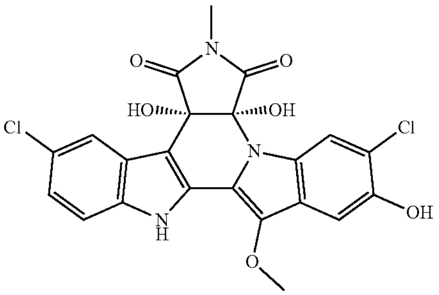

Lazarimide A;

-continued

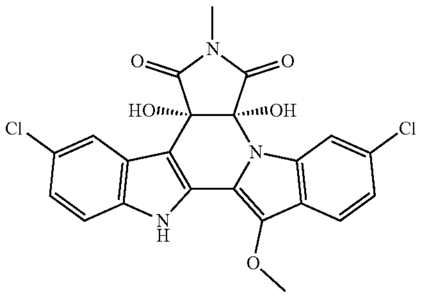

Lazarimide B;

BE-54017

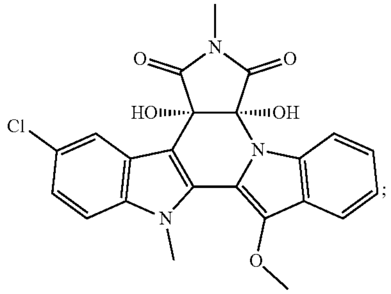

BE-54017'5

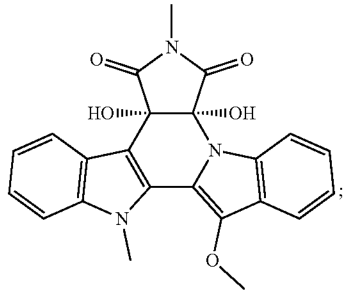

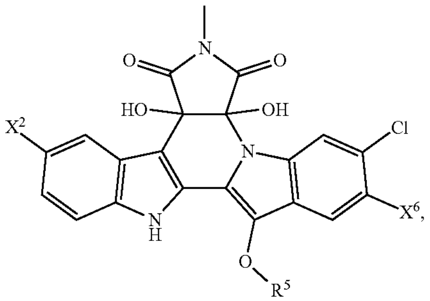

or wherein $R^5$ is $C_{1-4}$alkyl, $X^2$ is selected from H and halo, and $R^1$ is selected from H, halo and OH.

In an embodiment, $Z^1$, $Z^2$, $Z^3$, $Z^4$, $Z^5$, $Z^6$, $Z^7$, $X^1$, $X^2$, $Y^1$, $Y^2$, $Y^3$, $W^1$, $W^2$, $R^1$, R' and R" are as defined herein for the compound of Formula I so long as the compound is not exactly any of the structures shown hereinabove in the proviso for the compound of Formula I(b).

The present disclosure also includes a compound of Formula II:

II

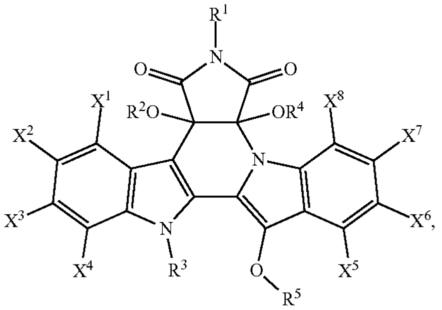

wherein $X^1$, $X^2$, $X^3$, $X^4$, $X^5$, $X^6$, $X^7$, and $X^8$ are each independently H, halo, optionally substituted alkyl, aryl, heteroaryl, $NO_2$, NR'R", $NR'S_2$, CONR'R", NR'COR", OR', SR', CN, or $CF_3$;

$R^1$, $R^2$, $R^3$, $R^4$, and $R^5$ are each independently H or an optionally substituted alkyl; and R' and R" are each independently H, or an optionally substituted alkyl;

or a pharmaceutically acceptable salt thereof, with the proviso that said compound is not exactly:

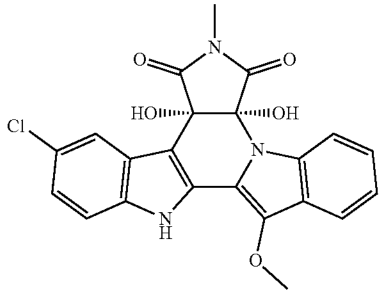

Cladoniamide A;

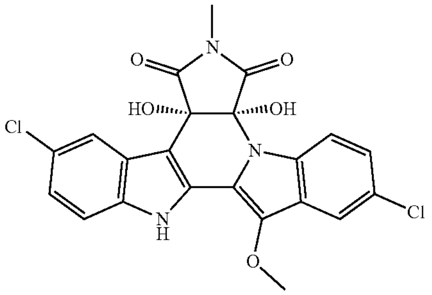

Cladoniamide B;

-continued

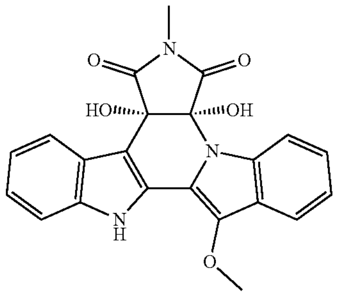

Cladoniamide C;

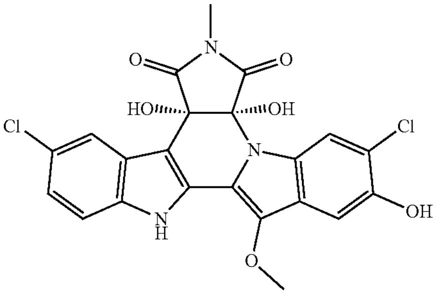

Lazarimide A;

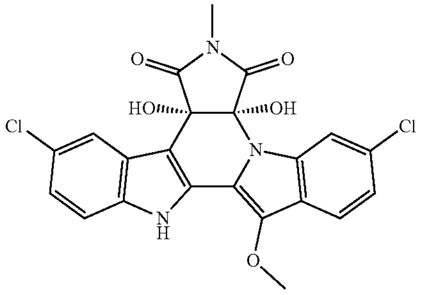

Lazarimide B;

BE-54017

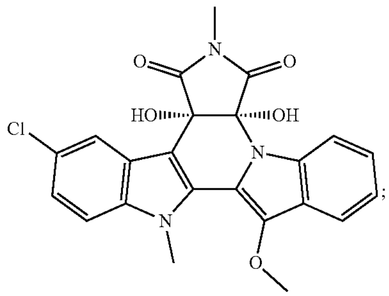

BE-54017'5

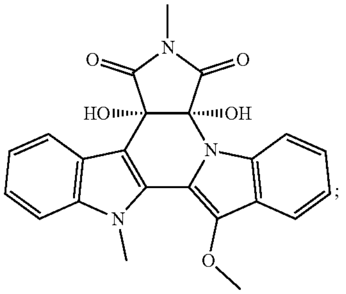

-continued

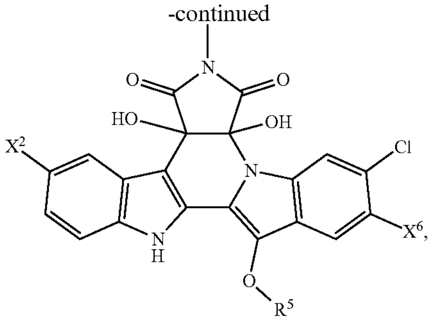

or wherein $R^5$ is $C_{1-4}$alkyl, $X^2$ is selected from H and halo, and $R^1$ is selected from H, halo and OH.

The present disclosure also includes a composition comprising one or more compounds (e.g. a compound of Formula I(b), Formula II or Formula II(a) as defined herein) and a carrier. The compounds are optionally formulated into pharmaceutical compositions for administration to subjects or use in a biologically compatible form suitable for administration and use in vivo. Accordingly, the present disclosure further includes a pharmaceutical composition comprising one or more compounds (e.g. a compound of Formula I(b), Formula II or Formula II(a) as defined herein) and a pharmaceutically acceptable carrier.

In an embodiment, the compound is a compound of Formula II and the compound is prepared, for example, by a method comprising the reactions shown in Scheme 1. In the compounds of Formulae II and IV to VIII, $X^1$-$X^8$ and $R^1$-$R^5$ are as defined herein. A skilled person could readily use and/or adapt such a method to prepare a compound of Formula I, Formula I(a), Formula I(b), Formula II(a), Formula III, Formula III(a) or Formula III(b).

Scheme 1
General synthetic scheme to obtain cladoniamide A and derivatives thereof.

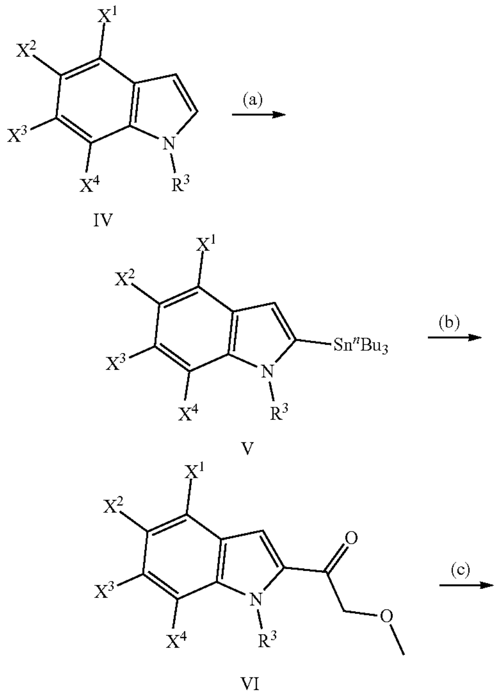

-continued

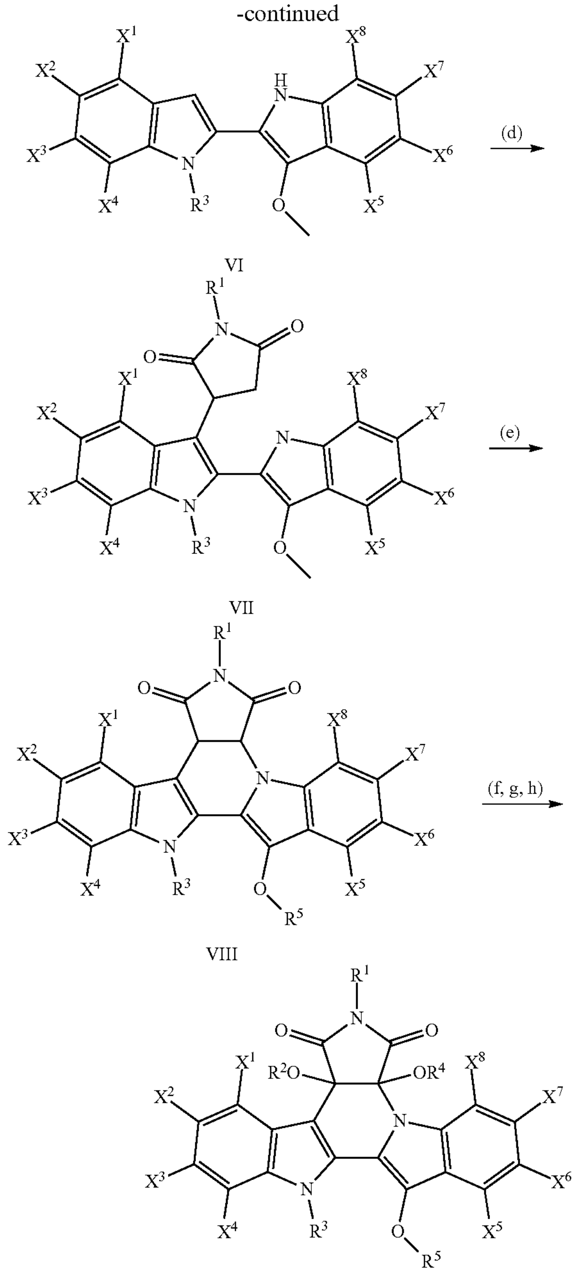

VI

VII

VIII

II

Exemplary reaction conditions for compounds such as cladoniamide A: (a) *J Org Chem* 1995 (60) 6218 [i) n-BuLi, THF, -66° C., ii) $CO_2$, iii) t-BuLi, iv) $nBu_3SnCl$, v) $NH_4Cl$, 5° C.]; (b) methoxyacetyl chloride, $Pd_2(dba)_3$, THF, DMF, 40° C.; 24 h; (c) $PhNHNH_2$, AcOH; 118° C., 1 h; (d) N-Me-maleimide, $SnCl_2$, toluene; 110° C., 24 h; (e) Pd black, nitrobenzene, 200° C., 1 h; (f) MeI, KOH, DMF, rt, 1 h (optional); (g) $OsO_4$, pyridine, 40° C., 12 h; (h) sat. $NaHSO_{3(aq)}$, 50° C., 6 h.

Various alternative embodiments and examples are described herein. These embodiments and examples are illustrative and should not be construed as limiting the scope of the invention. The following are non-limiting examples of the present disclosure:

EXAMPLES

Materials and Methods

The procedures described herein are given for the purposes of example and illustration only and should not be considered to limit the spirit or scope of the invention.

The cladoniamides used in these studies were obtained by fermentation and isolation based on a previous literature report by Williams et al. (2008). Cladoniamides may, for example, also be chemically synthesized or biosynthesized. For example, the chemical synthesis of cladoniamide A may follow a literature report by Kimura et al. (2012). The biosynthesis of cladoniamides may be based on a literature report by Du et al. (2014).

Cell culture. Vero E6 cells (ATCC #CCL-81), A549 cells (ATCC #CCL-185, or acquired from Synthego), and U87 MG cells (ATCC #HTB-14, or acquired from Synthego) were maintained in Minimum Essential Medium (MEM; Gibco) supplemented with 10% fetal bovine serum (FBS; Gibco), 1% non-essential amino acids (Gibco), and 1 mM sodium pyruvate (Gibco). Huh-7.5.1 cells and Huh-7.5 replicon-containing cells were cultured in Dulbecco's Modified Eagle's Medium (DMEM; Gibco) supplemented with 10% FBS (Gibco), 10 mM (4-(2-hydroxyethyl)-1-piperazineethanesulfonic acid) (HEPES; Gibco), and 1% non-essential amino acids (Gibco). The replicon-containing cells were maintained in the presence of 0.3 mg/mL gentamicin (Gibco). All incubations were performed at 37° C. in the presence of 5% $CO_2$ unless otherwise noted.

Viruses. ZIKV: ZIKV strain PRVABC59 (Puerto Rico/2015) (ATCC #VR-1843) was used in these studies, specifically three separate stocks generated in Vero E6 cells with titres of $1.35\times10^8$ pfu/mL, $1.0\times10^7$ pfu/mL, and $2.9\times10^6$ pfu/mL respectively. DENV strains: DENV-2 strain NGC, DENV-3 strain H-87, and DENV-4 strain H-241 were kindly provided by National Microbiology Laboratory, Winnipeg, MB, Canada.

Semisolid overlay plaque assays. Vero E6 cell monolayers were seeded in 12 well plates (Sarstedt) and incubated for 24 h. Supernatants of ZIKV infected cells were serially diluted starting at 1:100 and used to inoculate the cells for 1 h. Virus was then removed and plaque assay cultures were overlaid with 1% low melt agarose (Gibco) in minimum essential media (MEM; Gibco) supplemented with 2% heat inactivated FBS (Sigma-Aldrich Corp.), 1% non-essential amino acids (Gibco) and 1 mM sodium pyruvate (Gibco). The agarose overlay was melted and maintained at 42° C. before adding to the cells. Plaques were fixed after 5 days with 3.7% formaldehyde in PBS (Gibco) for 1 h, after which the overlay was removed, and plaques were visualized by staining with 1% crystal violet (Sigma-Aldrich Corp.) in 20% methanol.

Liquid overlay plaque assays. Vero E6 cell monolayers were seeded in 12 well plates (Sarstedt) and incubated for 24 h. Supernatants of ZIKV infected cells were serially diluted starting at 1:100 and used to inoculate the cells for 1 h. Virus was then removed and plaque assay cultures were overlaid with 1% microcrystalline cellulose (Avicel™ CL-611; DuPont) in MEM (Gibco) supplemented with 2% FBS (Gibco), 1% non-essential amino acids (Gibco) and 1 mM sodium pyruvate (Gibco). The overlay was removed, and plaques were fixed after 3 days with 3.7% formaldehyde in PBS (Gibco) for 1 h. Plaques were visualized by staining with 1% crystal violet (Sigma-Aldrich Corp.) in 20% methanol.

Example 1: Anti-ZIKV Activity

Figure 2:
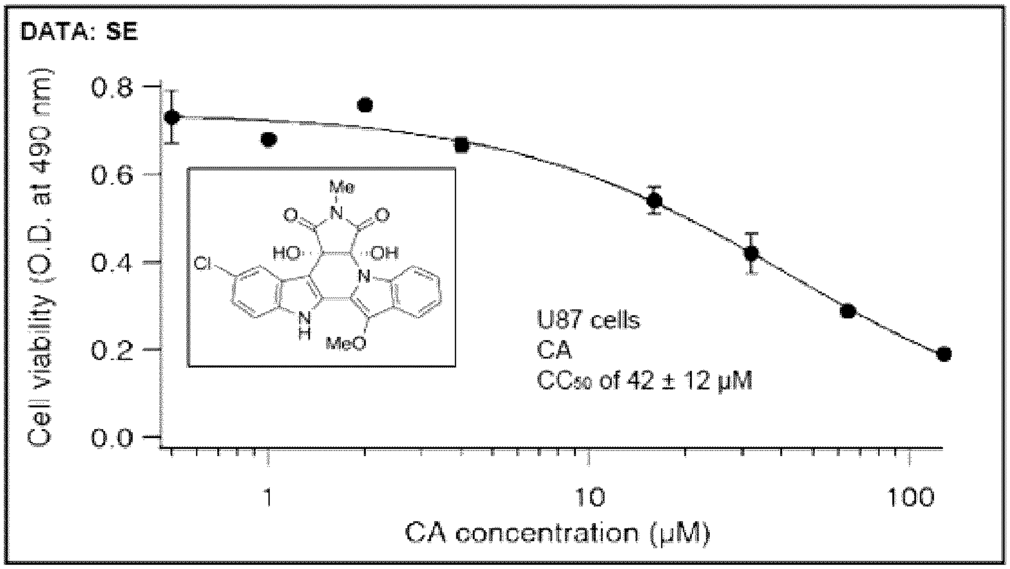
FIG. 2 is a plot to determine cytotoxicity concentration 50% ($CC_{50}$) of CA in U87 cells. Error bars represent SD among two biological replicates.

An MTS assay was performed to determine the cytotoxicity concentration 50% ($CC_{50}$) of cladoniamide A (CA) in human A549 cells, a cell line from human lung carcinoma. Various concentrations of CA were added to cultured A549 cells and incubated (37° C., 5% $CO_2$) for 48 h. Cell viability was then measured by an MTS assay kit (CellTiter 96™ Aqueous One Solution cell proliferation assay, Promega) according to the manufacturer's instructions. Curve fitting was performed in Igor Pro (WaveMetrics) using a hyperbolic fit algorithm (FIG. 1). The $CC_{50}$ of CA in A549 cells was determined to be 54±5 μM. An MTS assay was also performed to determine the $CC_{50}$ of CA in human U87 MG cells, a cell line from human brain. Various concentrations of CA were added to cultured U87 MG cells and incubated (37° C., 5% $CO_2$) for 48 h. Cell viability was then measured by an MTS assay kit (CellTiter 96 Aqueous One Solution cell proliferation assay, Promega) according to the manufacturer's instructions. Curve fitting was performed in Igor Pro (WaveMetrics) using a hyperbolic fit algorithm (FIG. 2). The $CC_{50}$ of CA in U87 MG cells was determined to be 42±12 μM.

Figure 3:
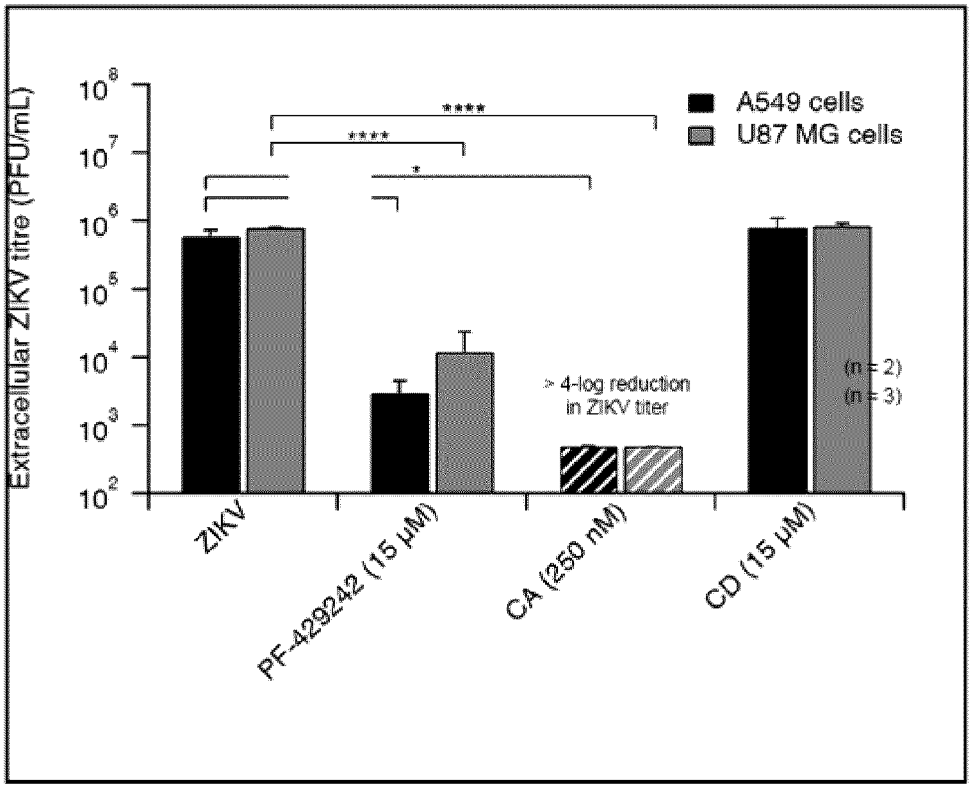
FIG. 3 is a plot showing that CA, but not cladoniamide D (CD), exhibits nanomolar antiviral activity against ZIKV. Average viral titres from two independent experiments (A549 cells) or three independent experiments (U87 MG cells) are shown. Significance was measured by a 2-tailed unpaired Student's t-test: *, $p<0.05$; ****, $p<0.0001$.

Cultured A549 and U87 MG cells were treated with CA (250 nM), cladoniamide D (CD; 15 μM), or PF-429242 (Hyrina 2017; 15 μM) for 1 h before being washed with PBS and inoculated with ZIKV at multiplicity of infection (MOI) 1.0 for 1 h. Following the removal of the inoculum, cells were incubated in fresh media for 3 d before the supernatant was collected, clarified, and ZIKV infectivity was measured by semisolid overlay plaque assay. Hatched bars representing limit of quantitation (LOQ) of the plaque assay are shown where values below LOQ were obtained (FIG. 3). There was a greater than 4-log reduction in ZIKV titer when A549 and U87 MG cells were treated with CA.

Figure 4:
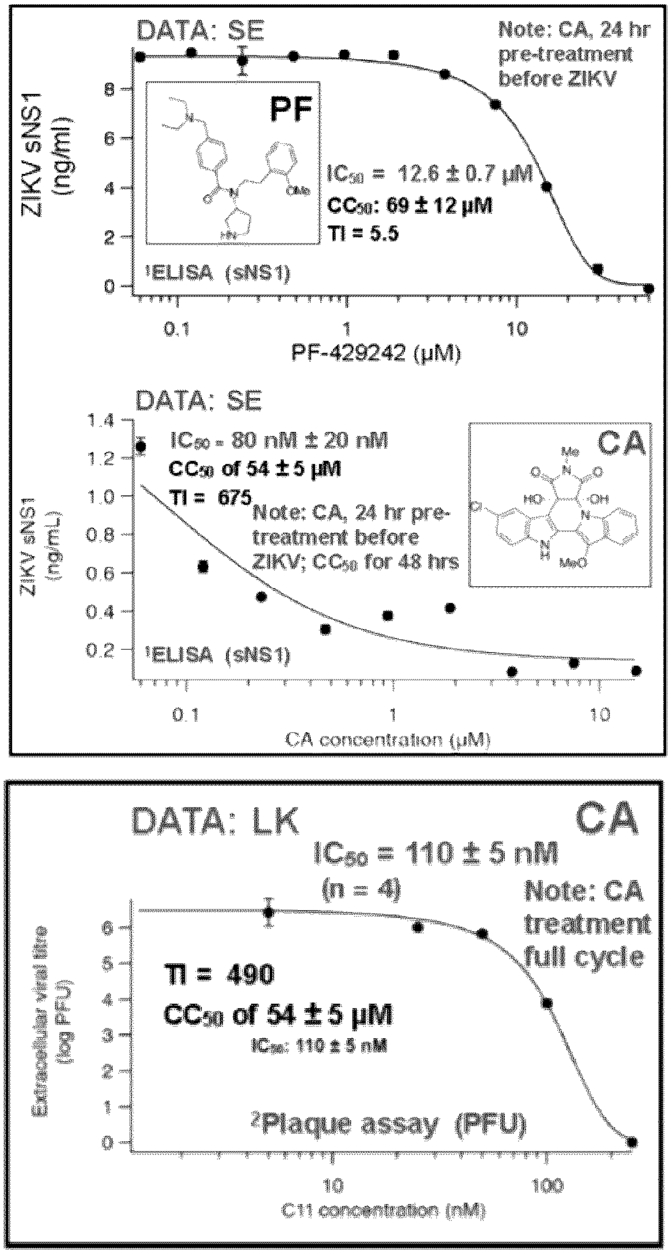
FIG. 4 shows $IC_{50}$ and therapeutic index (TI) values of PF-429242 (PF) and CA against ZIKV infection from extracellular viral NS1 enzyme-linked immunosorbent assay (ELISA) results (upper and middle plots, respectively) and $IC_{50}$ and TI values of CA from plaque assay (PFU) results (lower plot). Error bars represent SD among 2 biological replicates.

Cultured A549 cells were treated with various concentrations of CA or PF-429242 for 24 h before being washed with PBS and inoculated with ZIKV (ZIKV strain VR 1843, Puerto Rico, 2015; ATCC) at MOI 1.0 for 1 h. Following the removal of the inoculum, cells were incubated in fresh media for 2 d before the supernatant was collected, clarified, and secreted NS1 protein abundance was measured by an ELISA kit (BioFront Technologies) according to the manufacturer's instructions. Curve fitting was performed in Igor Pro (WaveMetrics) using a hyperbolic fit algorithm (FIG. 4; upper and middle plots) and $IC_{50}$ and TI values obtained. $IC_{50}$ and TI values were also obtained for CA via plaque assay (PFU; FIG. 4, lower plot). FIG. 4 (upper plot) is an $ED_{50}$ curve for the PF inhibitor based on the detection of secreted Non-Structural protein 1 (sNS1), secreted viral biomarker. sNS1 was detected using an Elisa test (commercially available). FIG. 4 (middle plot) is an $ED_{50}$ curve for CA based on the detection of secreted Non-Structural protein 1 (sNS1), secreted viral biomarker. sNS1 was detected using an Elisa test (commercially available).

Bottom: ED50 curve for CA based on the detection of secreted infectious virus particles, as viral biomarker. Titer of the infectious virus particles (Plaque forming units) determined using plaque assays. The results of these studies are summarized in Table 1.

TABLE 1

CA vs PF as anti-ZIKV agents in human A549 cells.

| IAA | $CC_{50}$ (μM) | $IC_{50}$ (μM) | TI |
|---|---|---|---|
| PF | 69 | 13* | 5.5 |
| CA | 54 | 0.08* | 675 |
| CA | 54 | 0.110** | 490 |

*ELISA (sNS1);
**Plaque assay (PFU).

Figure 5:
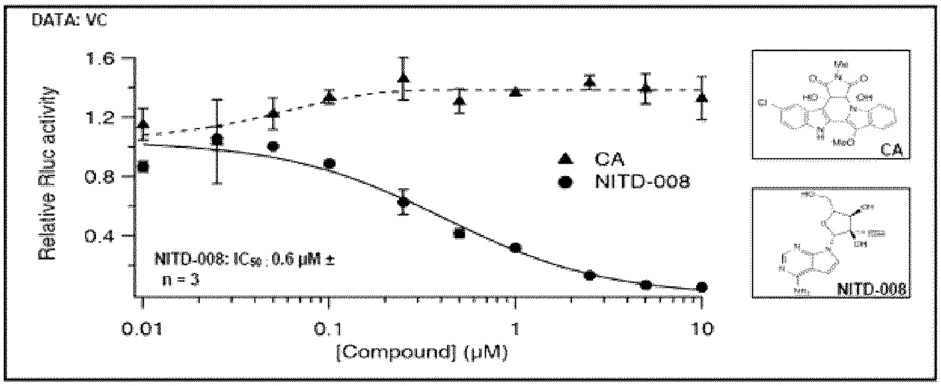
FIG. 5 shows that in contrast to NITD-008, CA is not a ZIKV replication inhibitor. Error bars represent SD among 3 biological replicates.

Cultured Huh-7.5.1 cells and Huh-7.5 ZIKV replicon-containing cells (Xie 2016) were treated with various concentrations of CA or putative ZIKV replication inhibitor NITD-008 (Deng 2016) for 48 h. Cells were then washed with PBS and ViviRen™ Live Cell Substrate (Promega) was added to a final concentration of 30 μM. Following incubation for 2 min at room temperature, luminescence was measured. Curve fitting was performed in Igor Pro (WaveMetrics) using a sigmoidal fit algorithm (FIG. 5). As can be seen from the results in FIG. 5, in contrast to NITD-008, CA is not a ZIKV replication inhibitor.

Figure 6:
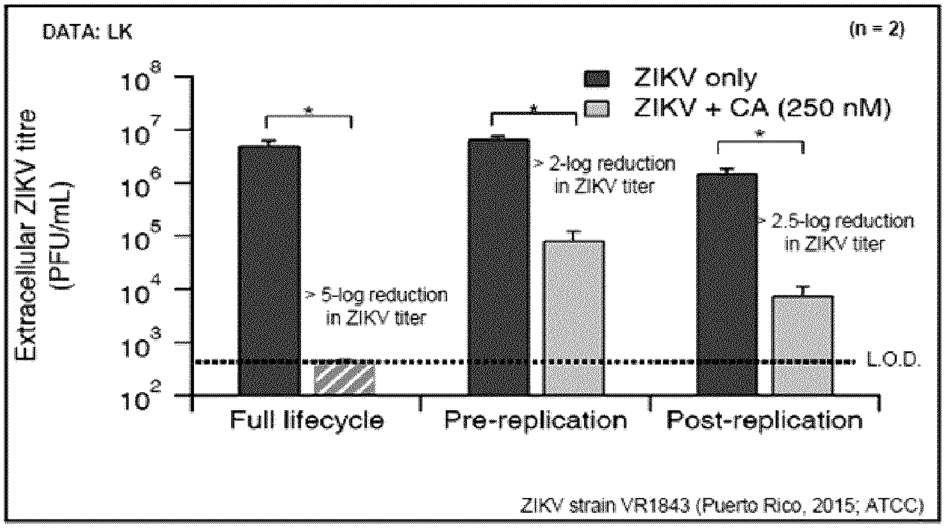
FIG. 6 shows that CA is dual inhibitor of ZIKV infection targeting the entry and maturation steps. Error bars represent SEM among 3 biological replicates. Significance was calculated by a 2-tailed unpaired Student's t-test. *, $p<0.05$.

Cultured A549 cells were inoculated with ZIKV for 1 h at MOI 1.0, and maintained for 2 d under different experimental conditions. For "Full lifecycle" 250 nM CA was added following the inoculation and maintained in the medium for 2 d; for "Pre-replication" 250 nM CA was added following the inoculation and maintained in the medium for 6 h, after which the cells were washed with PBS and the medium was changed; and for "Post-replication" 250 nM CA was added to the culture medium 12 hours post infection (hpi) and maintained until 24 hpi, after which the cells were washed with PBS and the medium was changed. Limit of detection (LOD) of the plaque assay is indicated in FIG. 6.

Cladoniamide A demonstrated good activity against ZIKV in vitro (FIG. 1-FIG. 6). While cladoniamide A dramatically inhibited the production of infectious ZIKV virions at 50 nm, cladoniamide D did not show any inhibitory effect (FIG. 3).

Figure 7:
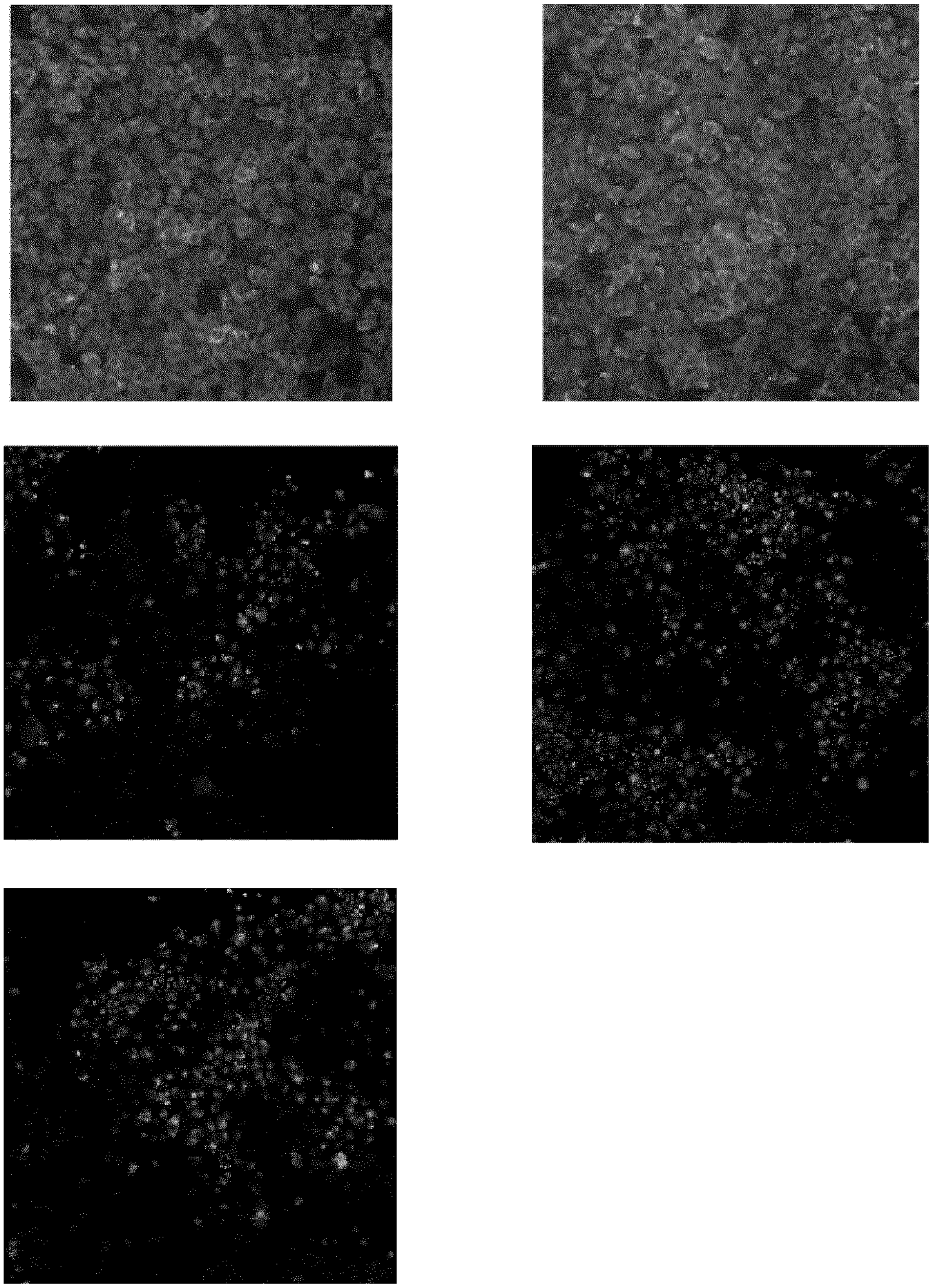
FIG. 7 shows results for CA (upper right image), cladoniamide D (CD; middle left image), cladoniamide E (CE; middle right image); and cladoniamide F (lower left image) in comparison to a control (upper left image). Cultured A549 cells were treated with 15 μM of the cladoniamide before being washed with PBS and infected with ZIKV at MOI 1.0 for 48 h. Cells were labeled for viral dsRNA then imaged using the Cellomics ArrayScan™ VTI.

A549 cells were seeded onto Corning tissue culture treated 96 well plates at 6500 cells/well (100 μL) and incubated at 37 degrees Celsius and 5% $CO_2$ for 24 h. CA, CD, cladoniamide E (CE) and cladoniamide F (CF) were diluted in MEM complete media to concentrations of 15 μM. The diluted CA, CD, CE or CF was added to the respective wells and cells were incubated at 37 degrees Celsius and 5% $CO_2$ for 1 h. After 1 h, cells were washed once with PBS to remove the CA, CD, CE or CF and were then infected with ZIKV at an MOI of 1. Cells were incubated with ZIKV for 48 h at 37 degrees Celsius and 5% $CO_2$. Cells were fixed with 3.7% formaldehyde in PBS then labeled with the J2 anti-dsRNA IgG2a monoclonal antibody (Scicons) at a concentration of 1:500. Cells were then labeled with the goat anti-mouse Alexa Fluor™ 488 (ThermoFisher) at 1:2000. Labeled 96 well plates were imaged and quantified using the Cellomics ArrayScan VTI. CA demonstrated good activity against ZIKV whereas CD, CE and CF did not show any inhibitory effect (FIG. 7).

Example 2: Anti-DENV Activity

Figure 8:
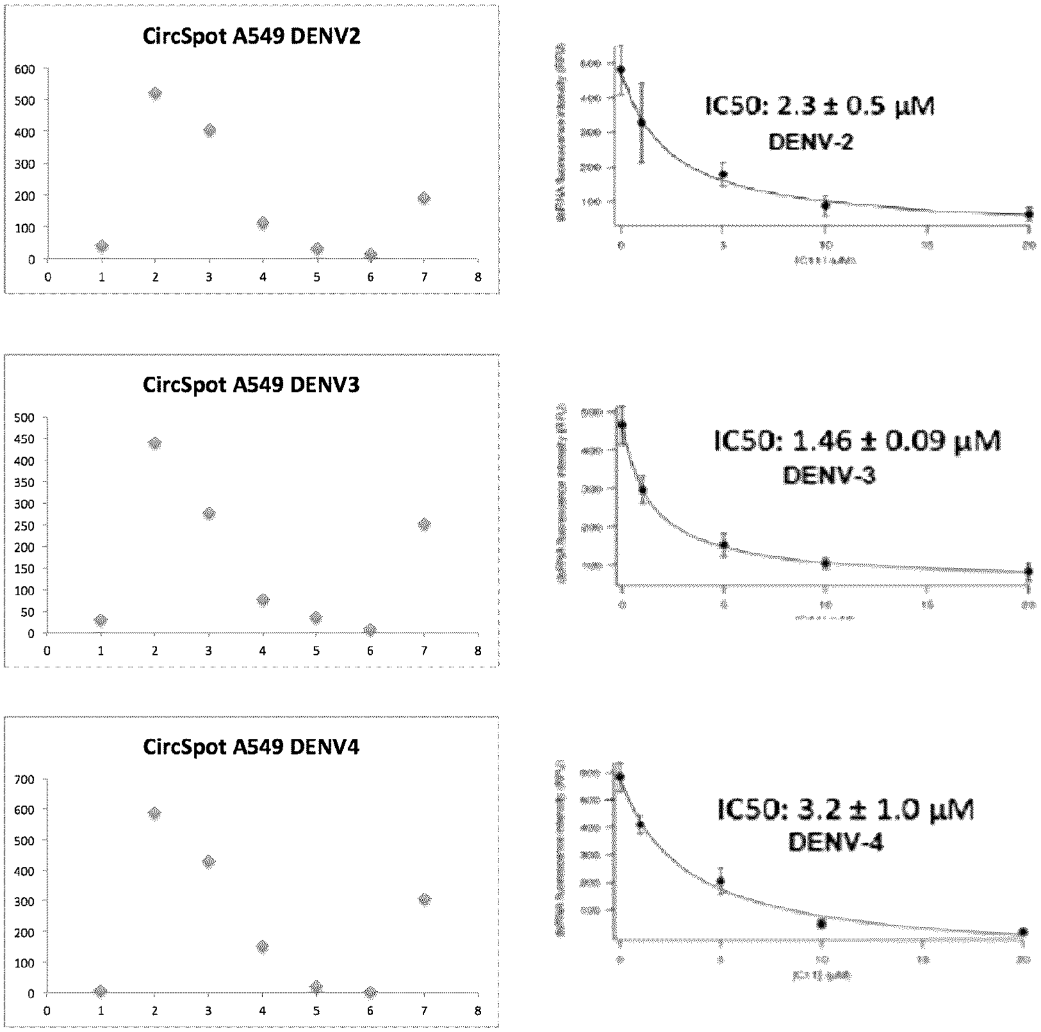
FIG. 8 shows results for DENV-2 (upper plots), DENV-3 (middle plots) and DENV-4 (lower plots), showing CA is a potential broad-spectrum anti-flavivirus agent. Error bars represent SD among 3 biological replicates. Cultured A549 cells were treated with the indicated concentrations of CA (1=Mock, 2=0 M, 3=1 μM, 4=5 M, 5=10 M, 6=20 M) or PF-429242 (7=15 M) for 1 h before being washed with PBS and infected with DENV-2, DENV-3, or DENV-4 at MOI 1.0 for 48 h. Cells were labeled for viral dsRNA with Hoechst dye then imaged and quantified using the Cellomics ArrayScan™ VTI High Content Screening system.

A549 cells were seeded onto Corning tissue culture treated 96 well plates and incubated at 37 degrees Celsius and 5% $CO_2$ for 24 h. CA was diluted in MEM complete media to concentrations of 1 μM, 5 μM, 10 μM, 20 μM, including a 0 μM condition. Diluted CA was added to each well and cells were incubated at 37 degrees Celsius and 5% $CO_2$ for 1 h. After 1 h, cells were washed once with PBS to remove CA and were then infected with DENV-2, -3 or -4 at an MOI of 1. Cells were incubated with DENV for 48 h at 37 degrees Celsius and 5% $CO_2$. Cells were fixed with 3.7% formaldehyde in PBS then labeled with the J2 anti-dsRNA IgG2a monoclonal antibody (Scicons) at a concentration of 1:500. Cells were then labeled with the goat anti-mouse Alexa Fluor™ 488 (ThermoFisher) at 1:2000 and Hoechst. Labeled 96 well plates were imaged and quantified using the Cellomics ArrayScan VTI. Curve fitting was performed in Igor Pro (WaveMetrics) using a hyperbolic fit algorithm. Cladoniamide A demonstrated good activity against Dengue virus 2 (FIG. 8, upper plots), Dengue virus 3 (FIG. 8, middle plots) and Dengue virus 4 (FIG. 8, lower plots) in vitro. Table 2 provides a summary of the results. A drug is generally considered to have a good safety profile if its TI is greater than 10 (Muller & Milton 2012).

TABLE 2

CA is a pan-serotype inhibitor against DENV in human A549 cells.

| DENV | $IC_{50}$ (μM) | TI |
|---|---|---|
| DENV-2 | 2.3* | 24 |
| DENV-3 | 1.5* | 36 |
| DENV-4 | 3.2* | 17 |

*$IC_{50}$ values calculated based on intracellular dsRNA (Cellomics); $CC_{50}$: 54 ± 5 μM.

Figure 9:
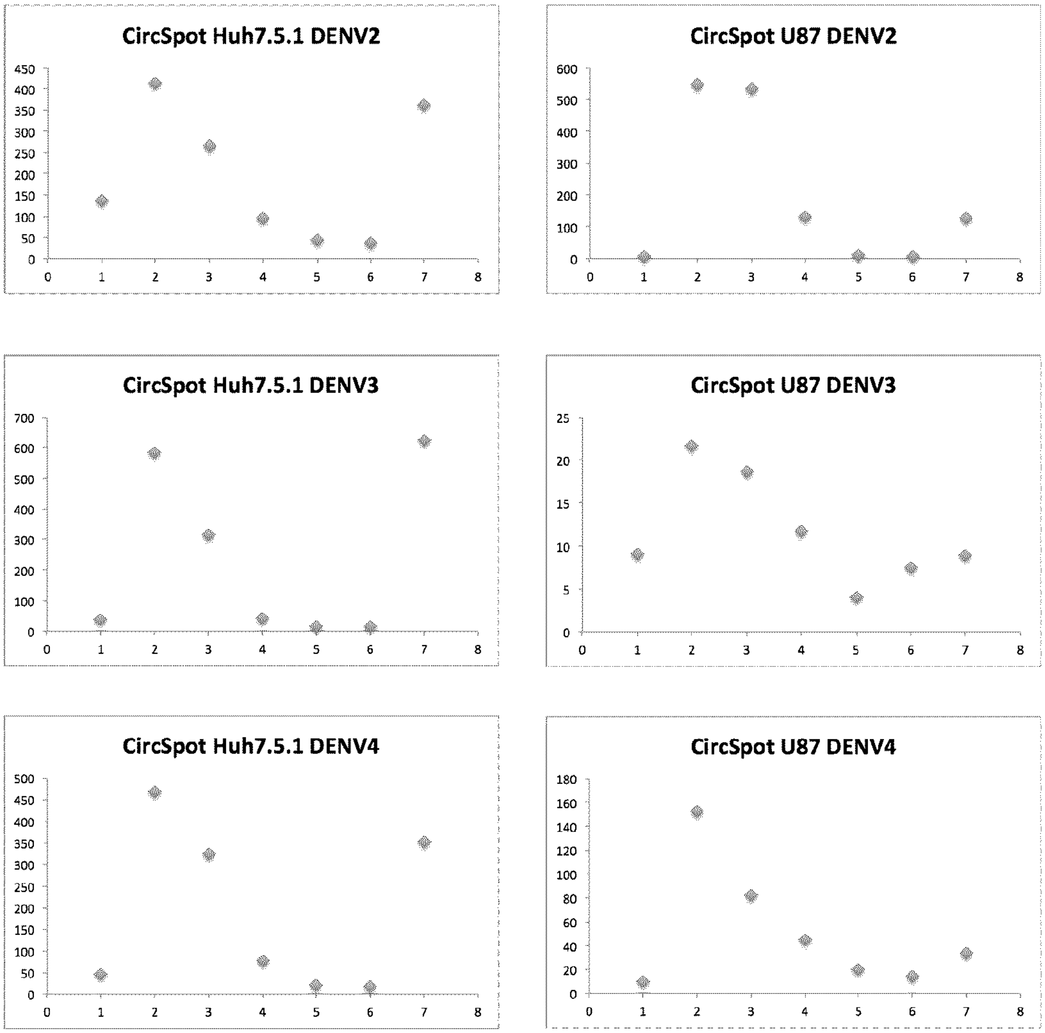
FIG. 9 shows results for DENV-2 (upper plots), DENV-3 (middle plots) and DENV-4 (lower plots), for Huh7.5.1 cells (left plots) and U87 cells (right plots) showing CA is a potential broad-spectrum anti-flavivirus agent. Cultured Huh7.5.1 cells (left plots) or U87 cells (right plots) were treated with the indicated concentrations of CA (1=Mock, 2=0 M, 3=1 M, 4=5 M, 5=10 M, 6=20 M) or PF-429242 (7=15 M) for 1 h before being washed with PBS and infected with DENV-2, DENV-3, or DENV-4 at MOI 1.0 for 48 h. Cells were labeled for viral dsRNA with Hoechst dye then imaged and quantified using the Cellomics ArrayScan™ VTI.

FIG. 9 shows similar results for Huh 7.5.1 cells (left plots) and U87 cells (right plots), against Dengue virus 2 (upper plots), Dengue virus 3 (middle plots) and Dengue virus 4 (lower plots) indicting the broad-spectrum anti-flaviviral activity of CA.

Example 3: V-ATPase Inhibitor Activity

Figure 10:
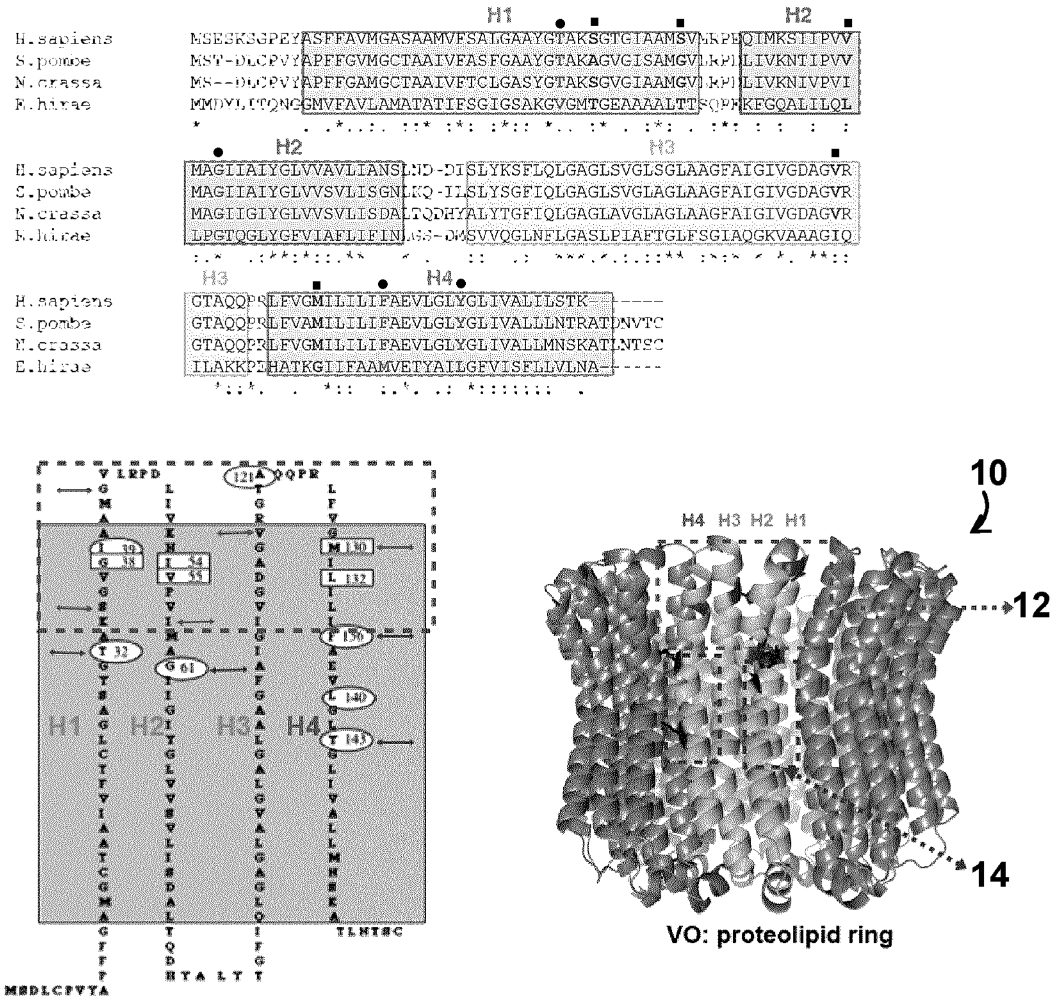
FIG. 10 shows molecular modelling of hVma3.

The crystal structure of the *E. hirae* ntpK V-type $Na^+$-ATPase is known (PDB 2BL2) (Murata 2005). *E. hirae* ntpK is homologous to *H. sapiens* ATP6V0C (Chang 2014). In the top image of FIG. 9, residues for which mutations associated with CA resistance have been found (■); and bafilomycin A1 resistance-associated mutations (●) are indicated (Chang 2014). FIG. 10 (lower left) is a schematic showing Vma3 topology and key amino acids, with the CA potential binding site indicated (dotted lines). The protein structure 10 of hVma3 (ATP6V0C) was visualized in PyMol (version 1.3; Schrodinger LLC) with one chain of the complex highlighted (FIG. 10, lower right). Referring to FIG. 10 (lower right) a CA potential binding site (5 specific amino acids) 12 and BAf1 binding site 14 are also indicated.

Figure 11:
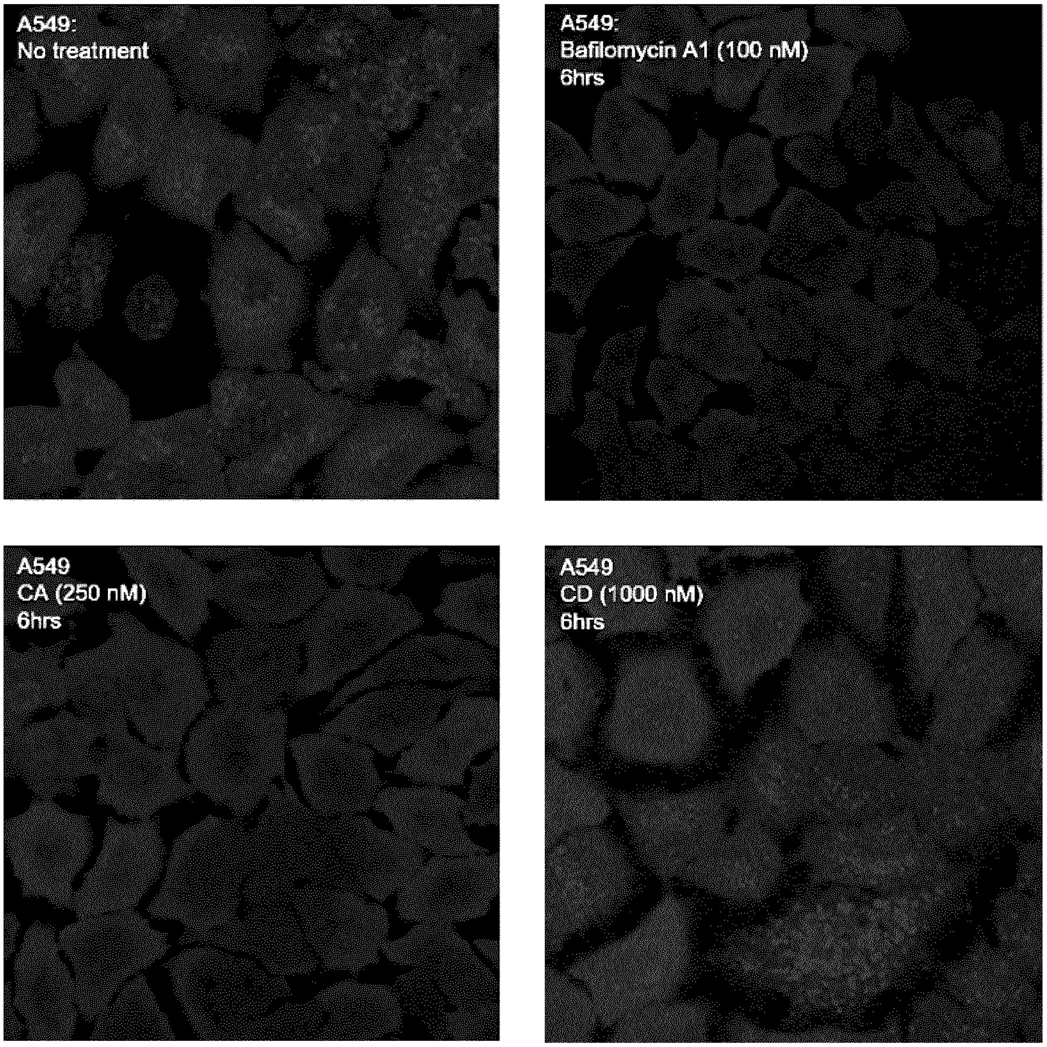
FIG. 11 shows fluorescence microscopy images of cultured A549 cells without treatment (upper left), and treated with Bafilomycin A1 (100 nM; upper right), CA (250 nM; lower left) and CD (1000 nM; lower right) for 6 hours then treated with acridine orange. CA but not CD inhibited vital staining with acridine orange of the intracellular organelles of the A549 cells.
Figure 12:
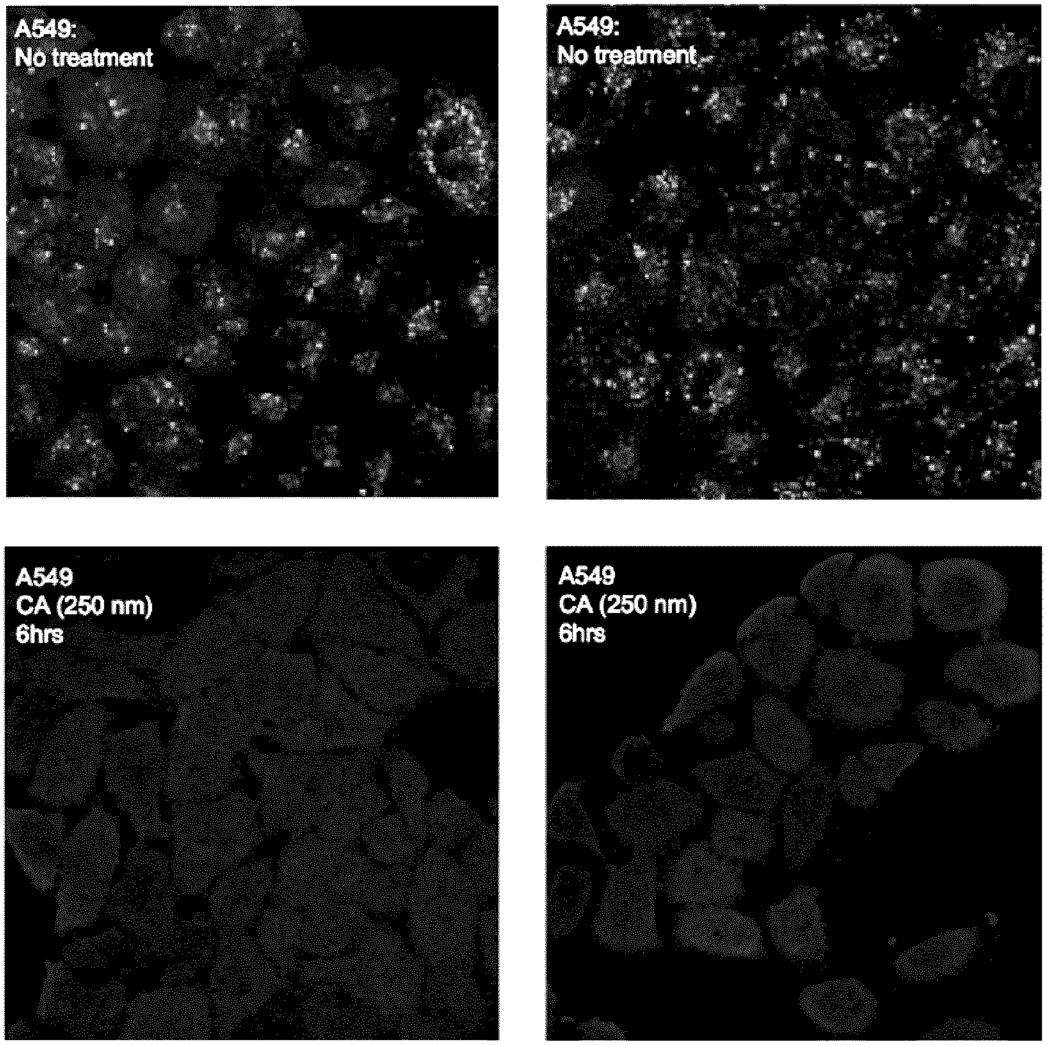
FIG. 12 shows additional fluorescence microscopy images of cultured A549 cells without treatment (upper left and right), and treated with CA (250 nM; lower left and right) for 6 hours then treated with acridine orange, showing CA activity as a V-ATPase inhibitor.
Figure 13:
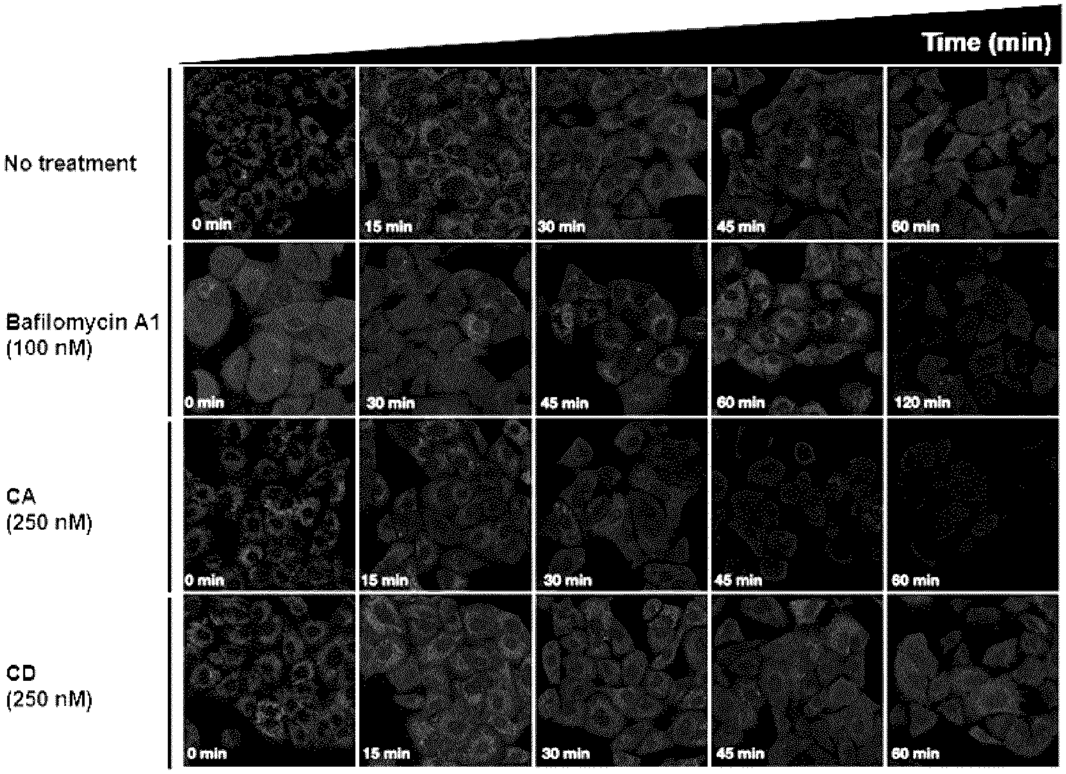
FIG. 13 shows fluorescence microscopy images of cultured A549 cells without treatment (top row), and treated with Bafilomycin A1 (100 nM; second row from top), CA (250 nM; second row from bottom) and CD (250 nM; bottom row) for the indicated time periods then treated with acridine orange, showing the time course of CA-mediated inhibition.

Cultured A549 cells were treated with 1 μM CD, or 250 nM CA or the V-ATPase specific inhibitor bafilomycin A1 (100 nm) for 6 h. After removing the culture medium and washing the cells with Hanks' balanced salt solution (HBSS), a 1:4000 dilution of acridine orange (2% solution, Polysciences Inc.) in HBSS was added to cells and incubated for 10 min. Cells were then washed again with HBSS and analyzed by fluorescence microscopy. In color images, a red color corresponds to the protonated version of the molecule, which permeates acidic organelles and becomes sequestered following protonation. One representative of 3 biological replicates is shown. FIG. 11 and FIG. 12 show results of the 6-hour treatment of A549 cells with the V-ATPase specific inhibitor bafilomycin A1 and cladoniamide A as well as cladoniamide D. Cladoniamide A, but not cladoniamide D, lead to intracellular pH dysregulation and inhibited vital staining with acridine orange of the intracellular organelles of human A549 cells. FIG. 13 shows results of the time course of treatment of A549 cells with bafilomycin A1, CA and CD.

Example 4: Anti-HcoV-229E Activity

Figure 14:
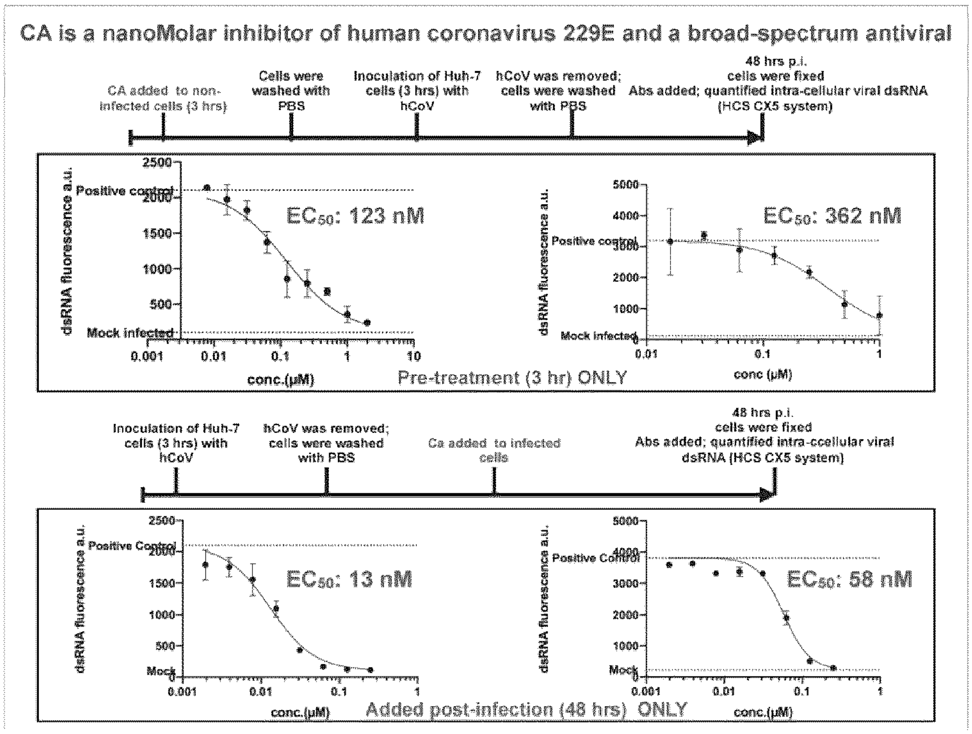
FIG. 14 shows the results of studies of cladoniamide A against human coronavirus 229E (HCoV-229E) in hepatoma cells (Huh 7.5 cells). An IF-based assay was used to monitor viral dsRNA in infected cells. CA inhibits HCoV-229E infections in human cells, acting as an indirect antiviral agent targeting human V-ATPase, $EC_{50}$=15 nM.

CA pre-treatment: Cladoniamide A was added to non-infected Huh-7 cells (3 h). Cells were washed with PBS and inoculated with human coronavirus 229E (HCoV-229E) for 3 hours, then HCoV-229E was removed and the cells were washed with PBS once more. 48 hours post-infection, the cells were fixed and the intra-cellular viral dsRNA was quantified (HCS CX5 system). The results are shown in FIG. 14 (top). CA added post-infection: Huh-7 cells were inoculated with HCoV-229E for 3 hours. Then HCoV-229E was removed and cells were washed with PBS. Cladoniamide A was added to these infected cells. 48 hours post-infection, the cells were fixed and the intra-cellular viral dsRNA was quantified (HCS CX5 system). The results are shown in FIG. 14 (bottom). The experiment was conducted in triplicate, and the average $EC_{50}$ value from these three independent experiments was $EC_{50}$=15 nM. These results show CA is a nanomolar inhibitor of HCoV-229E.

Example 5: Anti-SARS-CoV Activity

All infections were carried out in a Biosafety Level 3 (BSL3) facility (UBC FINDER) in accordance with the Public Health Agency of Canada and UBC FINDER regulations. SARS-CoV-2 (SARS-COV-2/Canada/VIDO-01/2020) was passaged in Vero E6 cells. For experiments, passage three of the virus was used with a determined viral titer of $1.5\times10^7$ plaque forming units (PFU)/mL. Calu-3 cells were seeded at a concentration of 10,000 cells/well in 96-well plates the day before infection. SARS-CoV-2 stocks were diluted in cell-specific media to a multiplicity of infection (MOI) of 2. Cells were pretreated with compounds for three hours and then incubated with the virus for 2 days, followed by fixation of the cells with 3.7% formalin for 30 min to inactivate the virus. The fixative was removed, cells were washed with PBS, and permeabilized with 0.1% Triton X-100 for 5 minutes, followed by immunostaining with the mouse primary antibody J2 (dsRNA) and rabbit primary antibody HL344 (SARS-CoV-2 nucleocapsid) at working dilutions of 1:1000 for 1 hour at room temperature. Secondary antibodies were used at a 1:2000 dilution and included the goat anti-mouse IgG Alexa Fluor 488 and goat anti-rabbit IgG Alexa Fluor 555 with the nuclear stain Hoechst 33342 at 1 μg/mL for 1 hour at room temperature in the dark. After washing with PBS, plates were kept covered in aluminum foil at 4° C. until imaging on a High Content Screening (HCS) platform (CellInsight™ CX7 HCS, Thermo Fisher Scientific) with a 10× objective, or a EVOS™ M7000 Imaging System (Thermo Fisher Scientific) with a 20× or 40× objective.

Figure 15:
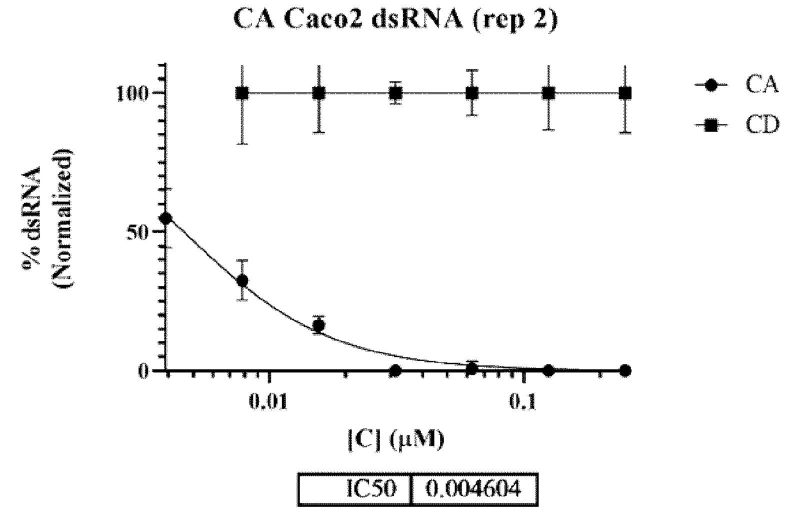
FIG. 15 shows plots of CA activity against SARS-CoV-2 in comparison to CD which showed no antiviral effect based on intracellular viral RNA (upper plot) and intracellular SARS-CoV-2 nucleocapsid protein (lower plot) in Human Caco2 cells pre-treated with the indicated amounts of CA or CD before adding the virus.
Figure 15:
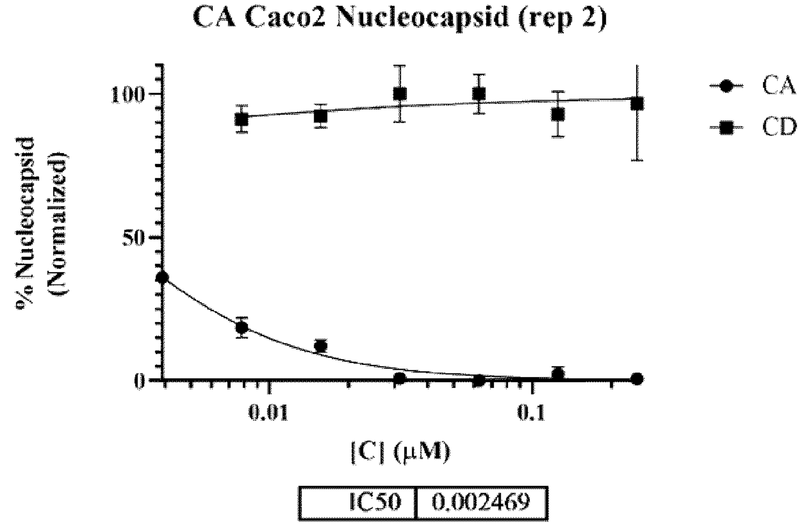

FIG. 15 shows data for CA activity against SARS-CoV-2. $ED_{50}$ values 2 of nM and 5 nM were obtained based on intracellular viral RNA (FIG. 15, upper plot) or intracellular SARS-CoV-2 nucleocapsid protein (FIG. 15, lower plot), respectively. In contrast, no antiviral effect of CD in Human Caco-2 cells against SARS-CoV-2 was detected (FIG. 15). In each, 3 hours pre-treatment of the cells was carried out with CA or CD before adding the virus. These results were in line with the data obtained for ZIKV and DENV. While not wishing to be limited by theory, the mechanism is V-ATPase regulation of intracellular pH.

Figure 16:
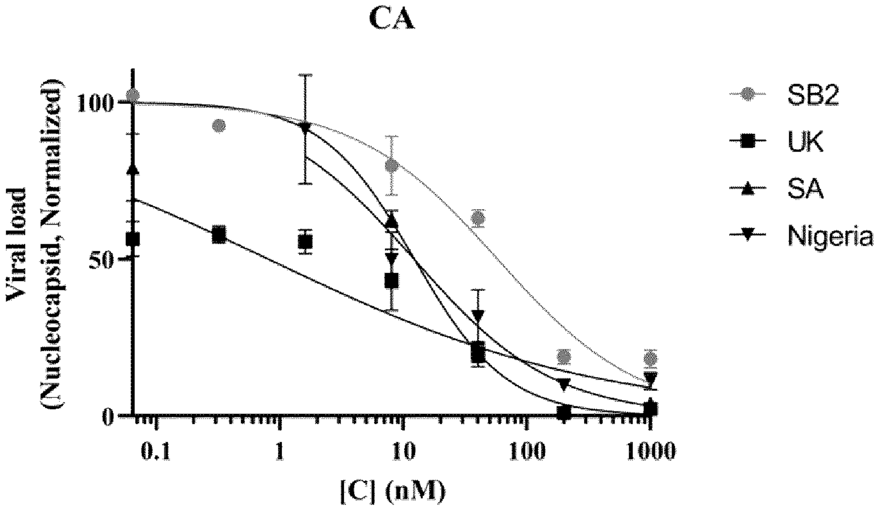
FIG. 16 is a plot of CA activity against the indicated SARS-CoV-2 variants based on intracellular SARS-CoV-2 nucleocapsid protein in human Calu-3 cells pre-treated with the indicated amounts of CA before adding the virus (n=1).

FIG. 16 shows results for SARS-CoV-2 Variants; namely SARS-CoV-2 Wuhan strain from VIDO (SB); SARS-CoV-2 England (VOC 202012/01) from BC-CDC (UK); SARS-CoV-2 South Africa (501Y.V2) from BC-CDC (SA); and SARS-CoV-2 Nigeria (484) (Nigeria). CA was observed to be a very potent antiviral for the SARS-CoV-2 Variants of Concern (VOCs) tested, namely SARS-CoV-2 South Africa (501Y.V2), SARS-CoV-2 UK (VOC 202012/01) and SARS-CoV-2 Nigeria. The $IC_{50}$ values are summarized in Table 3. Importantly, CA was found to be an 800 pM inhibitor of the UK variant ($ED_{50}$ 800 pM). Reports have suggested that the UK coronavirus variant is 70 percent more transmissible than the other variants. The UK variant has also been reported to be 64 percent deadlier than previous strains. These results also underline, for example, that CA and similar compounds may represent anew molecular tool to study CoV biology. For example, CA and similar compounds could permit the investigation of potential discrepancies in the viral hijacking of host-cell V-ATPase for new VOCs and/or unravel differences between the VOCs for usurping V-ATPase during the CoV infection. Further, such compounds may have broader applications in combating other widespread human enveloped viruses hijacking V-ATPases to support their lifecycles including pandemic H1N1 influenza A virus and highly pathogenic H5/H7 avian influenza A viruses.

TABLE 3 summary of $IC_{50}$ values for SARS-CoV-2 variants.

| | SB2 | UK | SA | Nigeria |
|---|---|---|---|---|
| $IC_{50}$ (nM) | 57.69 | 0.8010 | 12.25 | 12.17 |

Example 6: Anti-ZIKV Activity in Brain Organoids

Figure 17:
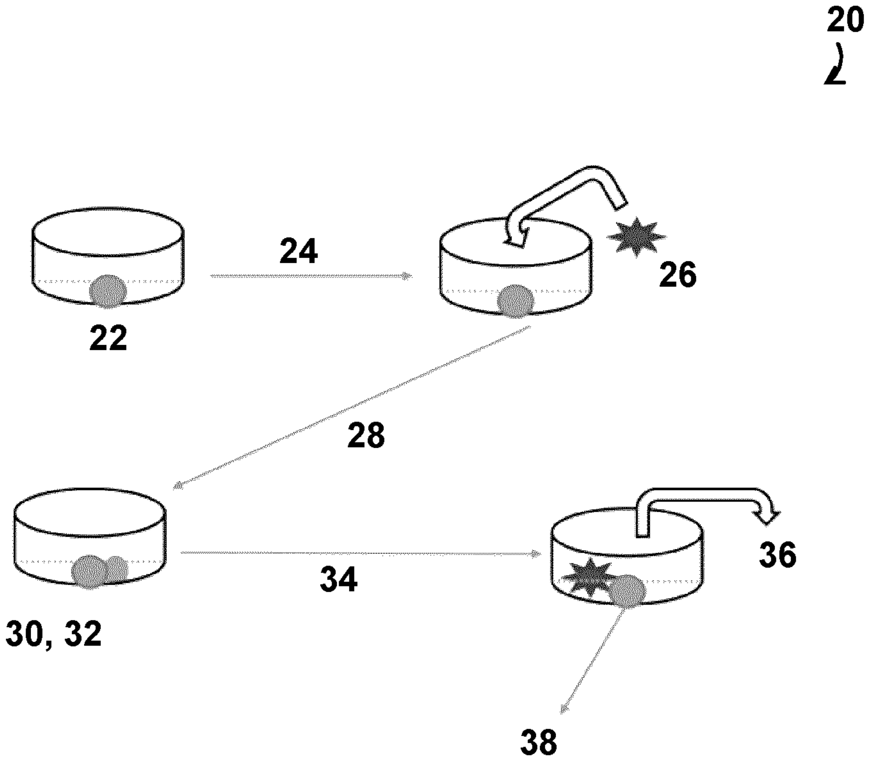
FIG. 17 is a schematic showing a general method used in the examples of the present disclosure to study treatment of brain organoids with CA or cladoniamide C (CC).

FIG. 17 is a schematic showing the general method 20 used in Example 6. Referring to FIG. 17, following growth of the brain organoids in STEMdiff™ media 22 (4 organoids/well), the media was aspirated 24. Then, 500 µL ZIKV at the desired MOI in fresh media was added 26 and the brain organoids incubated at 37° C. for 3 hours with gentle shaking 28. The brain organoids were then washed with 2×1 mL PBS 30, and fresh media and CA or cladoniamide C (CC) added to the desired concentration 32 prior to incubation for the desired time at 37° C. 34. The supernatant was collected and frozen at −86° C. 36 prior to analysis and the brain organoids transferred to an Eppendorf with paraformaldehyde for electron microscopy 38.

Figure 18:
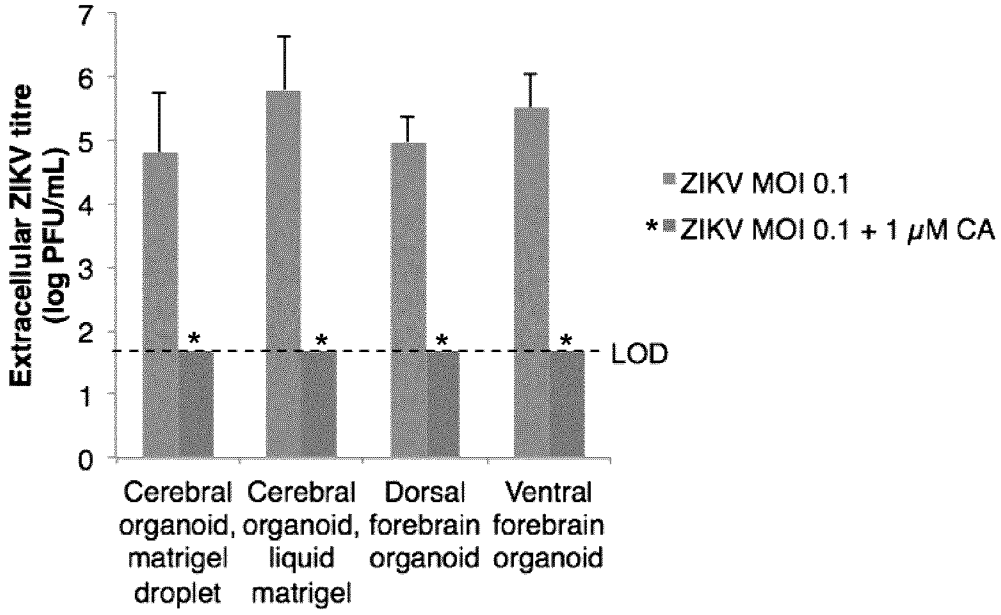
FIG. 18 is a plot showing extracellular ZIKV titer for four brain organoid systems after treatment with 1 μM CA for 72 hours in comparison to untreated controls.
Figure 19:
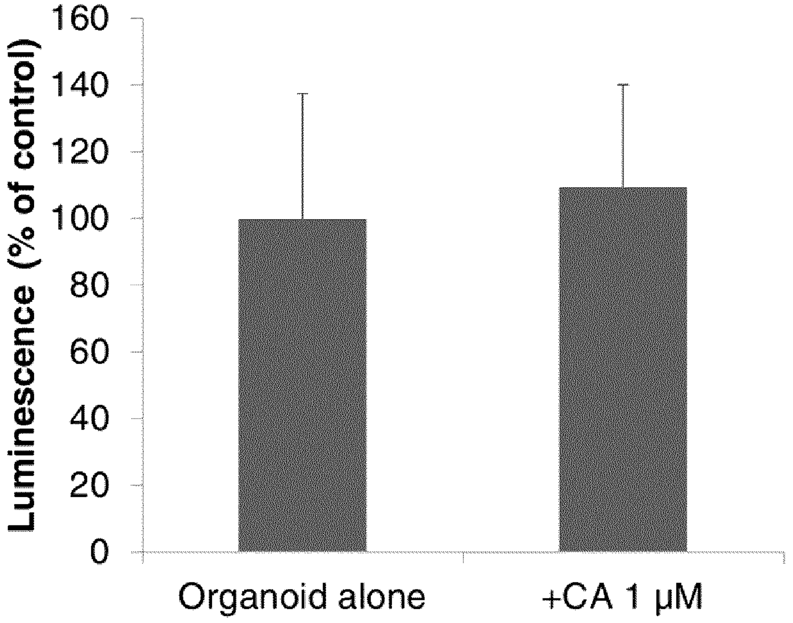
FIG. 19 is a plot showing toxicity results for brain organoids treated with 1 μM CA.
Figure 20:
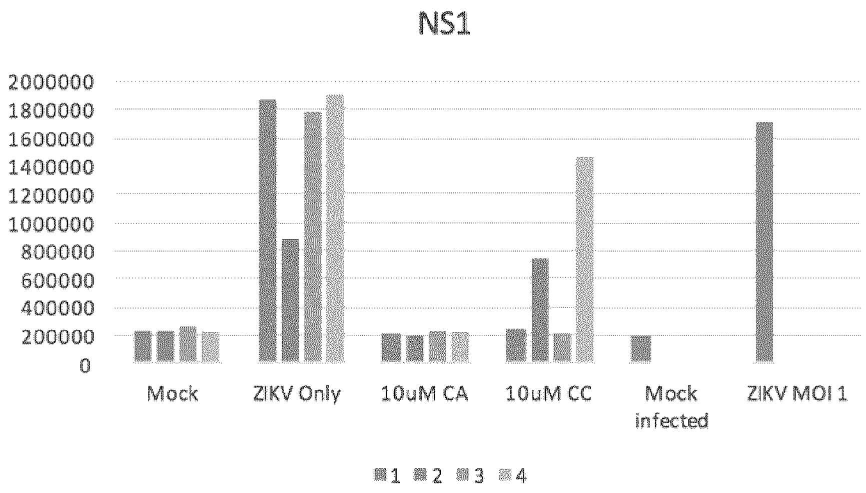
FIG. 20 shows plots of NS1 results for individual technical replicates (upper) and averaged values (lower) of brain organoids treated with 10 μM CA or CC for 69 hours.
Figure 20:
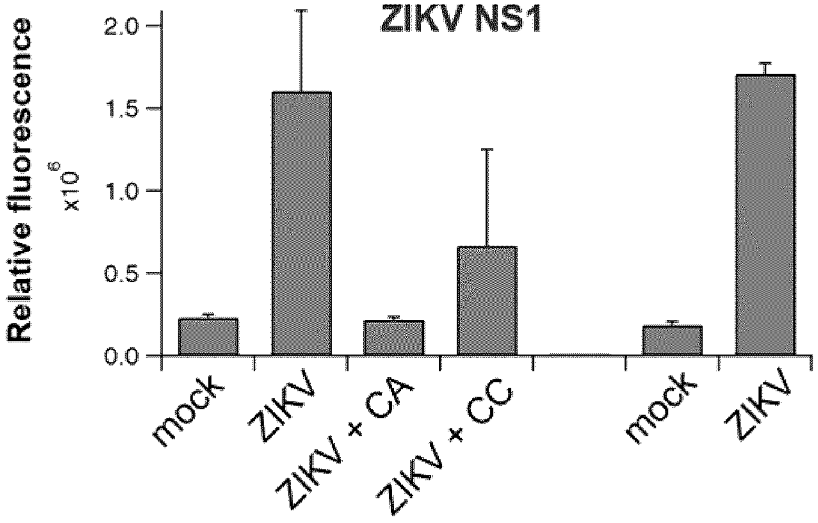
Figure 21:
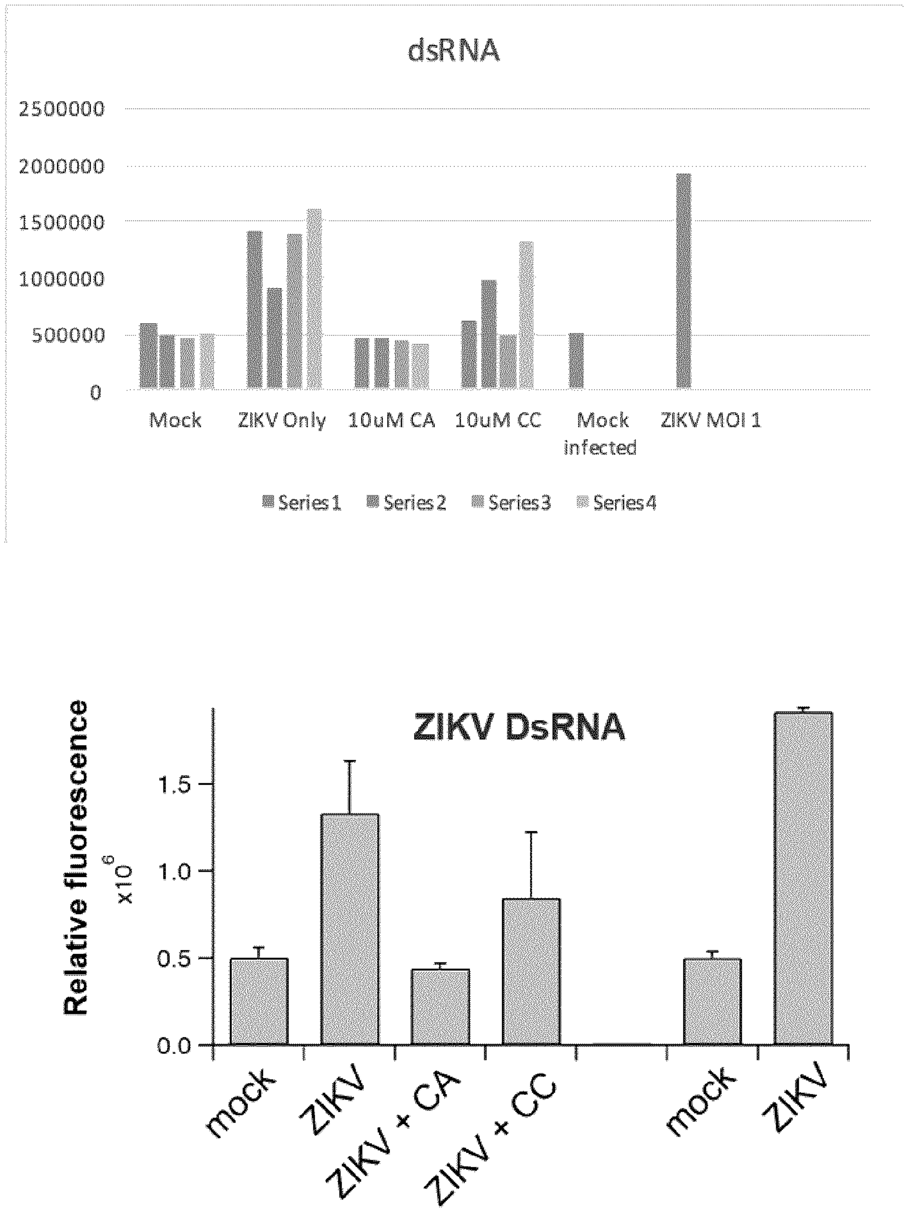
FIG. 21 shows plots of dsRNA results for individual technical replicates (upper) and averaged values (lower) of brain organoids treated with 10 μM CA or CC for 69 hours.

FIG. 18 is a plot showing the anti-ZIKV activity of cladoniamide A (incubation with 1 µM CA for 72 hours; 2 biological replicates, each with 4 organoids/well) using four brain organoid systems. There was a greater than 4-log reduction in extracellular ZIKV titer when treated with CA. A toxicity assay (CellTiter Glo™ 3D cell viability assay kit) showed CA is not toxic at 1 µM to brain organoids (FIG. 19). FIGS. 20 and 21 show plots showing the anti-ZIKV activity of CA and CC (incubation with 10 µM CA or CC for 69 hours, MOI 1; 4 technical replicates as there were 4 organoids/cell).

While the disclosure has been described with reference to what are presently considered to be the preferred examples, it is to be understood that the disclosure is not limited to the disclosed examples. To the contrary, the present disclosure is intended to cover various modifications and equivalent arrangements included within the spirit and scope of the appended claims. Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

REFERENCES

Citation of references herein is not an admission that such references are prior art to an embodiment of the present invention. The reference to any prior art in this specification is not, and should not be taken as, an acknowledgement or any form of suggestion that that prior art forms part of the common general knowledge in Canada or any other country. The invention includes all embodiments and variations substantially as hereinbefore described and with reference to the examples and drawings. Titles, headings, or the like are provided to enhance the reader's comprehension of this document, and should not be read as limiting the scope of the present invention. All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

F Y Chang, S A Kawashima, S F Brady: Mutations in the proteolipid subunits of the vacuolar H-ATPase provide resistance to indrolotryptoline natural products. *Biochem* 2014 (53) 7123.

Y Q Deng, N N Zhang, C F Li, M Tian, J N Hao, X P Xie, P Y Shi, C F Qin: Adenosine analog NITD008 is a potent inhibitor of zika virus. *Open Forum Infect Dis* 2016 (3,4):6.

Y L Du, D E Williams, B O Patrick, R J Andersen, K S Ryan: Reconstruction of cladoniamide biosynthesis reveals non-enzymatic routes to bisindole diversity. *ACS Chem Biol* 2014 (9) 2748.

R L Hudkins, J L Diebold, F D Marsh: Synthesis Of 2-aryl- and 2-vinyl-1H-indoles via palladium-catalyzed cross-coupling of aryl and vinyl halides with 1-carboxy-2-(tributylstannyl)indole. *J Org Chem* 1995 (60:19) 6218-6220.

A Hyrina, F Meng, S J McArthur, S Eivemark, I R Nabi, F Jean: Human Subtilisin Kexin Isozyme-1 (SKI-1)/Site-1 Protease (SIP) regulates cytoplasmic lipid droplet abundance: A potential target for indirect-acting anti-dengue virus agents. *PloS One* 2017 (12,3):e0174483.

T Kimura, S Kanagaki, Y Matsui, M Imoto, T Watanabe, M Shibasaki: Synthesis and assignment of the absolute configuration of indenotryptoline bisindole alkaloid BE-54017. *Org Lett* 2012 (14) 4418.

P Y Muller, M N Milton: The determination and interpretation of the therapeutic index in drug development. *Nat Rev Drug Discov.* 2012 (11) 751-61.

T Murata, I Yamato, Y Kakinuma, A Leslie, J Walker: Structure of the rotor of the V-type Na+-ATPase from *Enterococcus hirae*. *Science* 2005 (308) 654.

D W Williams, J Davies, B O Patrick, H Bottriell, T Tarling, M Roberge, R J Andersen:

Cladoniamides A-G, tryptophan-derived alkaloids produced in culture by *Streptomyces uncialis*. *Org Lett* 2008 (10) 3501.

X Xie, J Zou, C Shan, Y Yang, D Buh, K Dallmeier, J Neyts, P Y Shi: Zika Virus Replicons for Drug Discovery. *EbioMedicine* 2016 (12) 156.

S Brady, D Montiel: Indolotryptoline anticancer agents. Patent family WO 2017/004568.

X Deng, S P Duffy, M E Myrand-Lapierre, K Matthews, A T Santoso, Y L Du, K S Ryan: Reduced deformability of parasitized red blood cells as a biomarker for anti-malarial drug efficacy. *Malar J*2015 (14) 428.

Y L Du, K S Ryan: Expansion of bisindole biosynthetic pathways by combinatorial construction. *ACS Syn Biol* 2015 (4) 682.

H Hofmann, K Hattermann, A Marzi, T Gramberg, M Geier, M Krumbiegel, S Kuate, K Überla, M Niedrig, S Pohlmann: S-protein of severe acute respiratory syndrome-associated coronavirus mediates entry into hepatoma cell lines and is targeted by neutralizing antibodies in infected patients. *J Virol* 2004 (78) 6134.

C W Lin, F J Tsai, L Wan, C C Lai, K H Lin, T H Hsieh, S Y Shiu, J Y Li: Binding interaction of SARS coronavirus 3LC protease with vacuolar-H ATPase Gi subunit. *FEBS Lett* 2005 (579) 6089.

T Merino-Ramos, N Jimenez de Oya, J C Saiz, M A Martin-Acebes: Antiviral activity of nordihydroguiaretic acid and its derivative tetra-O-methyl nordihydrohuiaretic acid against West Nile virus and Zika virus. *Antimicrob Agent Chemother* 2017 (61) e00376-17.

The invention claimed is:

1. A method of treating a viral infection in a subject having the viral infection, wherein the viral infection is caused by one or more coronavirus, flavivirus, and/or influenza virus, the method comprising administering a compound of Formula I or a pharmaceutically acceptable salt thereof to the subject:

I

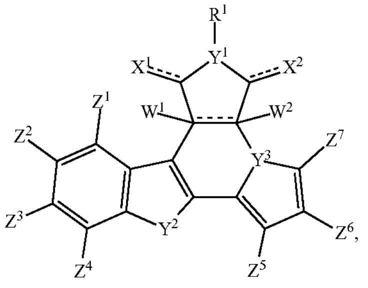

wherein each ----- independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

2. The method of claim 1, wherein the compound of Formula I is a compound of Formula I(a):

I(a)

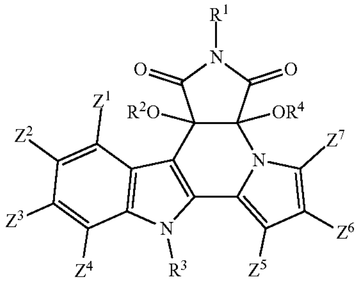

wherein $Z^1$, $Z^2$, $Z^3$, $Z^4$, $Z^5$, $Z^6$, and $Z^7$, are each independently H, halo, optionally substituted alkyl, aryl, heteroaryl, $NO_2$, NR'R", NR'$SO_2$R", CONR'R", NR'COR", OR', SR', CN, or $CF_3$; or $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$;

$R^1$, $R^2$, $R^3$, and $R^4$ are each independently H or an optionally substituted alkyl; and R' and R" are each independently H, or an optionally substituted alkyl.

3. The method of claim 2, wherein:

$R^1$ is $C_{1-6}$alkyl;

$Z^5$ is OR', wherein R' is alkyl;

$Z^2$ is halo or H; and $Z^6$ and $Z^7$ together form a substituted or unsubstituted aromatic ring.

4. The method of claim 3, wherein:

$R^1$ is methyl;

$Z^5$ is $OCH_3$;

$Z^2$ is chloro; and $Z^6$ and $Z^7$ together form an unsubstituted, 6-membered aromatic ring.

5. The method of claim 2, wherein $R^2$ and $R^4$ are both H.

6. The method of claim 2, wherein $R^3$ is H.

7. The method of claim 2, wherein $Z^1$, $Z^3$ and $Z^4$ are all H.

8. The method of claim 1, wherein the compound is a compound of Formula III:

III

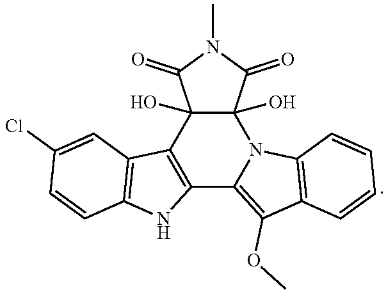

9. The method of claim 8, wherein the compound or pharmaceutically acceptable salt thereof is cladoniamide A.

10. The method of claim 1, wherein the viral infection is caused by one or more coronavirus and/or flavivirus.

11. The method of claim 10, wherein the viral infection is caused by one or more coronavirus.

12. The method of claim 11, wherein the viral infection is caused by one or more of severe acute respiratory syndrome (SARS) coronavirus-1 (SARS-COV-1), SARS coronavirus-2 (SARS-COV-2), Middle East respiratory syndrome (MERS) coronavirus (MERS-COV) and human coronavirus 229E (HCoV-229E).

13. The method of claim 12, wherein the viral infection is caused by SARS-CoV-2.

14. The method of claim 10, wherein the viral infection is caused by one or more flavivirus.

15. The method of claim 14, wherein the viral infection is caused by one or more of dengue virus (DENV), West Nile virus (WNV), Zika virus (ZIKV), Powassan virus (POWV), Japanese encephalitis virus (JEV) and yellow fever virus (YFV).

16. The method of claim 1, wherein the subject is a human.

17. A method of inhibiting vacuolar-$H^+$ATPase (V-ATPase), wherein the inhibition of V-ATPase is in a subject suffering from a viral infection, the method comprising contacting the V-ATPase with a compound of Formula I or a pharmaceutically acceptable salt thereof:

I

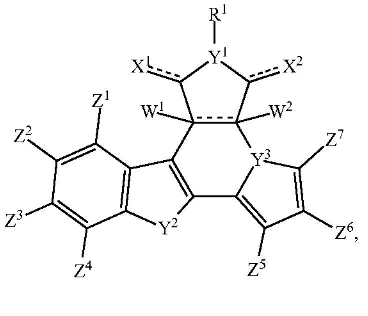

wherein each ----- independently represents a single or double bond;

$Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted; or one or more of $Z^1$ and $Z^2$, $Z^2$ and $Z^3$, $Z^3$ and $Z^4$, $Z^5$ and $Z^6$ and $Z^6$ and $Z^7$ together form an optionally substituted carbocyclic or heterocyclic ring, and the remainder of $Z^1$, $Z^2$, $Z^3$, $Z^4$, $Z^5$, $Z^6$, and $Z^7$ are each independently H, halo, alkyl, cycloalkyl, alkylene-aryl, aryl, heteroaryl, $NO_2$, NR'R", NR'$SO_2$R", $CO_2$R', COR', $CS_2$R', CSR', CONR'R", NR'COR", CSNR'R", NR'CSR", OR', SR', $SO_2$R', SOR', $SO_2$NR'R", CN or haloalkyl, wherein the alkyl, cycloalkyl, alkylene-aryl, aryl and heteroaryl are optionally substituted;

$X^1$ and $X^2$ are each independently O, H or OR';

$Y^1$ is N or CR';

$Y^2$ is NR', S, O or CR';

$Y^3$ is N or CR';

$W^1$ and $W^2$ are both absent or are each independently H, OR', NR' or SR';

$R^1$ is H or an optionally substituted alkyl; and

R' and R" are each independently H or an optionally substituted alkyl or alkylene-aryl.

18. The method of claim 17, wherein the subject is a human.

19. The method of claim 1, wherein the compound is formulated for administration in a pharmaceutical composition comprising the compound and optionally a pharmaceutically acceptable carrier.

20. The method of claim 17, wherein the compound is formulated for administration in a pharmaceutical composition comprising the compound and optionally a pharmaceutically acceptable carrier.

21. The method of claim 17, wherein the compound of Formula I is a compound of Formula I(a):

I(a)

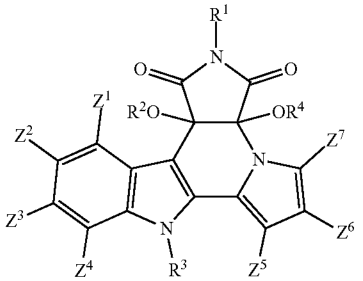

wherein $Z^1$, $Z^2$, $Z^3$, $Z^4$, $Z^5$, $Z^6$, and $Z^7$, are each independently H, halo, optionally substituted alkyl, aryl, heteroaryl, $NO_2$, NR'R", NR'$SO_2$R", CONR'R", NR'COR", OR', SR', CN, or $CF_3$; or $Z^6$ and $Z^7$ together form an optionally substituted aromatic ring, and $Z^1$, $Z^2$, $Z^3$, $Z^4$, and $Z^5$ are each independently H, halo, optionally substituted alkyl, aryl, heteroaryl, $NO_2$, NR'R", NR'$SO_2$R", CONR'R", NR'COR", OR', SR', CN, or $CF_3$;

$R^1$, $R^2$, $R^3$, and $R^4$ are each independently H or an optionally substituted alkyl; and R' and R" are each independently H, or an optionally substituted alkyl.

22. The method of claim 17, wherein the compound or pharmaceutically acceptable salt thereof is cladoniamide A.

* * * * *